(12) United States Patent
Arbuthnot et al.

(10) Patent No.: US 6,797,719 B2
(45) Date of Patent: Sep. 28, 2004

(54) BENZOTHIOPHENES, FORMULATIONS CONTAINING SAME, AND METHODS

(75) Inventors: Gordon Nelson Arbuthnot, Indianapolis, IN (US); Brian Weston Dalder, West Lafayette, IN (US); Kerry John Hartauer, Indianapolis, IN (US); Wayne Douglas Luke, West Lafayette, IN (US); Robert Eugene Stratford, Jr., Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 93 days.

(21) Appl. No.: 10/235,617

(22) Filed: Sep. 5, 2002

(65) Prior Publication Data

US 2003/0187025 A1 Oct. 2, 2003

Related U.S. Application Data

(63) Continuation of application No. 08/812,896, filed on Mar. 10, 1997, now Pat. No. 6,458,811.
(60) Provisional application No. 60/014,167, filed on Mar. 26, 1996.

(51) Int. Cl.[7] ............................................. A61K 31/445
(52) U.S. Cl. ...................... 514/324; 424/451; 424/463; 424/464; 424/474; 424/490
(58) Field of Search ........................ 514/324; 424/451, 424/463, 464, 474, 490

(56) References Cited

U.S. PATENT DOCUMENTS

| | | | |
|---|---|---|---|
| 4,133,814 A | 1/1979 | Jones et al. | 514/324 |
| 4,391,755 A | 7/1983 | Wang et al. | 552/514 |
| 4,418,068 A | 11/1983 | Jones | 514/324 |
| 4,515,805 A | 5/1985 | Newman | 514/460 |
| 4,605,517 A | 8/1986 | Riley et al. | 540/52 |
| 5,202,129 A | 4/1993 | Samejima et al. | 424/489 |
| 5,441,964 A | 8/1995 | Bryant et al. | 514/324 |
| 5,494,920 A | 2/1996 | Glasebrook et al. | 514/324 |
| 5,494,923 A | 2/1996 | Grese | 514/443 |
| 5,532,254 A | 7/1996 | Bowling | 514/320 |
| 5,629,425 A | 5/1997 | Labell et al. | 546/202 |
| 5,731,327 A | 3/1998 | Luke | 514/324 |
| 5,811,120 A * | 9/1998 | Gibson et al. | 424/464 |
| 6,458,811 B1 * | 10/2002 | Arbuthnot et al. | 514/324 |

FOREIGN PATENT DOCUMENTS

| | | |
|---|---|---|
| CA | 2141999 | 9/1995 |
| EP | 108606 A1 | 11/1983 |
| EP | 605193 A1 | 12/1993 |
| EP | 670162 A1 | 2/1995 |
| EP | 674903 A1 | 10/1995 |
| GB | 2293382 | 3/1996 |

OTHER PUBLICATIONS

Lieberman, et al., "Pharmaceutical Dosage Forms" Marcek Dekker Inc., p107–117, 186–187, 1980.
Omelczuk, et al., "Influence of micronization on the compaction properties of an investigational drug using tableting index analysis" Eur. J. Pharm. Biopharm., v. 43, 95–1 OC., 1997.
Jones, J.Med. Chem., 27:1057–1066, 1984.
Pharmaceutics, Chief Editor: Mr. XiNiao Zhu, the People's Health Publishers, third edition, Jul. 1994.

* cited by examiner

Primary Examiner—Ceila Chang
(74) Attorney, Agent, or Firm—Gilbert T. Voy; James J. Sales

(57) ABSTRACT

This invention provides compounds of formula I

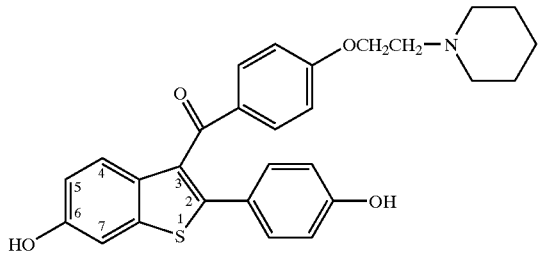

and pharmaceutically acceptable salts and solvates thereof, characterized that the compound is in particulate form and having a specific size range.

The present invention further provides pharmaceutical compositions containing or formulated using compounds of formula I, and the use of such compounds for alleviating human pathologies, including osteoporosis, serum lipid lowering, and breast cancer.

73 Claims, No Drawings

BENZOTHIOPHENES, FORMULATIONS CONTAINING SAME, AND METHODS

This application is a continuation of U.S. Ser. No. 08/812,896, filed Mar. 10, 1997 now U.S. Pat. No. 6,458,811, which claims priority to U.S. Ser. No. 60/014,167, filed Mar. 26, 1996.

FIELD OF THE INVENTION

This invention relates to the fields of pharmaceutical and organic chemistry and provides a benzothiophene compound, in particulate form, which is useful for the treatment of various medical indications, including osteoporosis and lipid lowering. More particularly, the benzothiophene is of a particle size range which allows enhanced bioavailability and control during the manufacturing process.

BACKGROUND OF THE INVENTION

Osteoporosis describes a group of diseases which arise from diverse etiologies, but which are characterized by the net loss of bone mass per unit volume. The consequence of this loss of bone mass and resulting bone fracture is the failure of the skeleton to provide adequate structural support for the body. One of the most common types of osteoporosis is that associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among post-menopausal women.

There are an estimated 25 million women in the United States, alone, who are afflicted with this disease. The results of osteoporosis are personally harmful and also account for a large economic loss due its chronicity and the need for extensive and long term support (hospitalization and nursing home care) from the disease sequelae. This is especially true in more elderly patients. Additionally, although osteoporosis is not generally thought of as a life threatening condition, a 20% to 30% mortality rate is related with hip fractures in elderly women. A large percentage of this mortality rate can be directly associated with post-menopausal osteoporosis.

At this time, the only generally accepted methods for treatment of post-menopausal osteoporosis are estrogen replacement therapy and the use of the bisphosphonate alendronate. Although therapy is generally successful, patient compliance with the therapy is relatively low primarily, due to undesirable side effects.

Throughout premenopausal time, most women have less incidence of cardiovascular disease than age-matched men. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that post-menopausal women having estrogen replacement therapy have a return of serum lipid levels to concentrations to those of the pre-menopausal state. Thus, estrogen would appear to be a reasonable treatment for this condition. However, the side-effects of estrogen replacement therapy are not acceptable to many women, thus limiting the use of this therapy. An ideal therapy for this condition would be an agent which would regulate the serum lipid level as does estrogen, but would be devoid of the side-effects and risks associated with estrogen therapy.

Preclinical findings with a structurally distinct "anti-estrogen", raloxifene, have demonstrated potential for improved selectivity of estrogenic effects in target tissues. Similar to tamoxifen, raloxifene was developed originally for treatment of breast cancer; however, the benzothiophene nucleus of raloxifene represented a significant structural deviation from the triphenylethylene nucleus of tamoxifen. Raloxifene binds with high affinity to the estrogen receptor, and inhibits estrogen-dependent proliferation in MCF-7 cells (human mammary tumor derived cell line) in cell culture. In vivo estrogen antagonist activity of raloxifene was furthermore demonstrated in carcinogen-induced models of mammary tumors in rodents. Significantly, in uterine tissue raloxifene was more effective than tamoxifen as an antagonist of the uterotrophic response to estrogen in immature rats and, in contrast to tamoxifen, raloxifene displayed only minimal uterotrophic response that was not dose-dependent in ovariectomized (OVX) rats. Thus, raloxifene is unique as an antagonist of the uterine estrogen receptor, in that it produces a nearly complete blockage of uterotrophic responses of estrogen due to minimal agonist effect of raloxifene in this tissue. Indeed, the ability of raloxifene to antagonize the uterine stimulatory effect of tamoxifen was recently demonstrated in OVX rats. Raloxifene is more properly characterized as a Selective Estrogen Receptor Modulator (SERM), due to its unique profile.

Raloxifene is now in Phase III clinical trials for osteoporosis. Indications thus far from these trials and other data, point to raloxifene's potential not only as an osteoporosis therapy, but also of potential use in lowering LDL (serum lipid) levels, inhibiting endometriosis and uterine fibrosis, and preventing breast cancer. The advancement of raloxifene has been somewhat hampered by its physical characteristics, both as to bioavailability and in manufacturing. For example, it is generally insoluble, and this can adversely affect the bioavailability. Clearly, any improvement in the physical characteristics of raloxifene, would potentially offer a more beneficial therapy and enhanced manufacturing capability.

SUMMARY OF THE INVENTION

This invention provides a compound of formula I

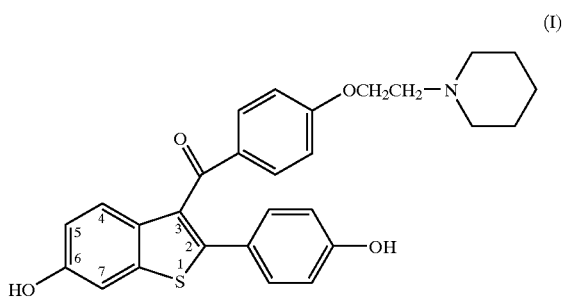

(I)

and pharmaceutically acceptable salts and solvates thereof, characterized in that the compound is in particulate form, said particles having a mean particle size of less than about 25 microns, and preferably between about 5 and about 20 microns.

Further, the present invention encompasses compounds of formula I wherein at least 90% of the particles have a particle size of less than about 50 microns, and preferably less than about 35 microns.

The present invention further relates to pharmaceutical compositions containing or formulated using one or more compounds of formula I, optionally containing estrogen or progestin, and the use of such compounds, alone, or in combination with estrogen or progestin, for alleviating the symptoms of osteoporosis lowering lipid levels, and inhibiting endometriosis, uterine fibrosis, and breast cancer.

DETAILED DESCRIPTION OF THE INVENTION

It has now been found that by processing compounds of formula I, to bring their particle size within a specified narrow range, pharmaceutical compositions may be prepared which exhibit for their active ingredient both a consistent in vitro dissolution profile and in vivo bioavailability. In addition to bringing about these desired dissolution/ bioavailability characteristics, the control of particle size to a narrow range has also resulted in significant improvements in manufacturing capabilities.

The mean particle size of the compounds of formula I, as set out by the invention, is less than about 25 microns, preferably between about 5 and about 20 microns. Further, the invention encompasses formula I compounds with at least 90% of the particles having a particle size of less than about 50 microns, preferably less than about 35 microns. More preferably, the mean particle size range is between about 5 and about 20 microns, with at least 90% of the particles having a size of less than about 35 microns.

It will of course be understood by those familiar with comminution process techniques that the limit set on the size of 90% or more of the particles is a limitation to further distinguish the particulate compounds of the invention from those exhibiting a broader size distribution, because of the wide variation in size encountered in all matter reduced in size by a process of comminution or particle size reduction, for example, by milling utilizing a variety of kinds of milling equipment now available, for example, hammer, pin or fluid energy mills.

The invention also provides pharmaceutical compositions comprising or formulated using the said particulate compound of the invention and one or more pharmaceutically-acceptable excipients or carriers.

The term "inhibit" is defined to include its generally accepted meaning which includes prohibiting, preventing, restraining, and lowering, stopping, or reversing progression or severity, and such action on a resultant symptom. As such the present invention includes both medical therapeutic and prophylactic administration, as appropriate.

The term "molar equivalents," as used herein, refers to the number of moles of the boron trihalide reagent in relation to the number of moles of the starting benzothiophene compound. For example, three millimoles of boron trichloride reacted with one millimole of the benzothiophene compound would represent three molar equivalents of boron trichloride.

The term "solvate" represents an aggregate that comprises one or more molecules of the solute, such as a formula I compound, with a molecule of solvent. Representative solvates are formed with methylene chloride, 1,2-dichloroethane, chloroform, and 1,2,3-trichloropropane.

A desirable form of raloxifene hydrochloride is the non-solvated crystalline form described in UK published patent application GB 2293382(A), published Mar. 27, 1996, filed Aug. 18, 1995, Application Number 9519028.6, incorporated herein by reference.

As used herein, the term estrogen includes steroidal compounds having estrogenic activity such as, for example, 17β-estradiol, estrone, conjugated estrogen (Premarin®), equine estrogen, 17β-ethynyl estradiol, and the like. As used herein, the term "progestin" includes compounds having progestational activity such as, for example, progesterone, norethylnodrel, nongestrel, megestrol acetate, norethindrone, and the like.

The term "mean particle size" is defined as equivalent spherical diameter as determined by laser light diffraction scattering.

Raloxifene's chemical name is 6-hydroxy-2-(4-hydroxyphenyl)-3-[4-(2-piperidinoethoxy)benzoyl]benzo[b]-thiophene. "Raloxifene" also encompasses the salts and solvates thereof, with the hydrochloride salt being preferred.

Raloxifene is a nuclear regulatory molecule or second generation selective estrogen receptor modulator (SERM). Raloxifene has been shown to bind to the estrogen receptor and was originally thought to be a molecule whose function and pharmacology was that of a pure anti-estrogen in that it blocked the ability of estrogen to activate uterine tissue and estrogen dependent breast cancers. Indeed, raloxifene does block the action of estrogen in some cells; however in other cell types, raloxifene activates the same genes as estrogen does and displays the same pharmacology, e.g., osteoporosis, hyperlipidemia. The unique profile which raloxifene displays and differs from that of estrogen is now thought to be due to the unique activation and/or suppression of various gene functions by the raloxifene-estrogen receptor complex as opposed to the activation and/or suppression of genes by the estrogen-estrogen receptor complex. Therefore, although raloxifene and estrogen utilize and compete for the same receptor, the pharmacological outcome from gene regulation of the two is not easily predicted and is unique to each.

The compounds of the current invention can be made according to established procedures, such as those detailed in U.S. Pat. Nos. 4,133,814, 4,418,068, and 4,380,635, and European Patent Application 95306050.6, Publication No. 0699672, Kjell, et al., filed Aug. 30, 1995, published Mar. 6, 1996, all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above.

Also, the information disclosed in the published European Patent Application number 0670162 A1, published on Sep. 6, 1995, is incorporated by reference.

A preferred synthesis is set out as follows. $R^4$ is hydrogen or $C_1-C_4$ alkoxy, $R^5$ is hydrogen or $C_1-C_4$ alkyl, and $R^6$ is chloro, bromo, or hydroxyl. HX is HCl or HBr.

The Formula II and III compounds, the starting materials for the compounds of formula I, are prepared using standard synthetic organic methods. The Formula II starting compound is readily obtained by a synthesis which is exemplified below in Preparation I and outlined in Scheme I.

Scheme I

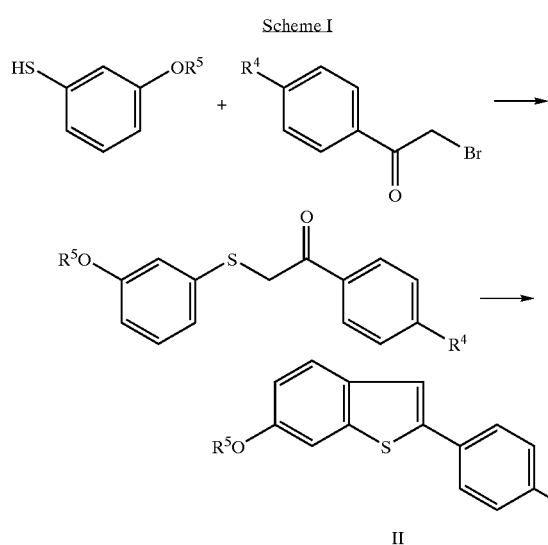

The Formula II compounds, wherein $R^4$ and $R^5$ are as defined above, are prepared by first reacting a 3-alkoxybenzenethiol with phenacyl or 4'-alkoxyphenacyl bromide in the presence of a strong base. Suitable bases for this transformation include, but are not limited to, potassium hydroxide and sodium hydroxide. The reaction is typically carried out in ethanol or a mixture of water and ethanol at a temperature of about 0° C. to about 50° C. The next step is cyclization of the arylphenacylsulfide. The cyclization is conveniently carried out by heating the arylphenacylsulfide in polyphosphoric acid. The cyclization is typically carried out at a temperature of about 80° C. to about 120° C., preferably between 85° C. and 90° C. The Formula II benzothiophene is typically purified by recrystallization. For example, when $R^4$ is methoxy and $R^5$ is methyl, the formula II compound may be recrystallized from ethyl acetate.

The acylating agent for the present process, a Formula III compound, is prepared as shown in Scheme II, wherein the variables $R^6$ and HX are as defined above and R is $C_1$–$C_4$ alkyl.

Scheme II

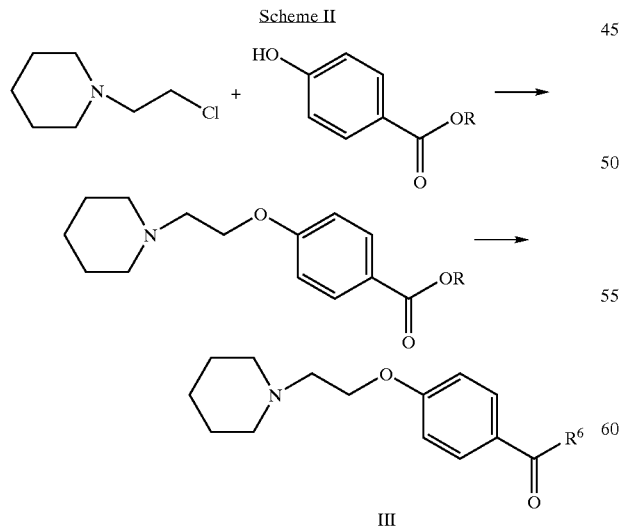

Generally, a $C_1$–$C_4$ alkyl 4-hydroxybenzoate is alkylated with a chloroethylamine in the presence of an inorganic base and the ester group hydrolyzed to produce the Formula III compounds, wherein $R^6$ is hydroxyl. Suitable inorganic bases for this alkylation include potassium carbonate and sodium carbonate. Suitable solvents for this alkylation are non-reactive polar organic solvents such as methyl ethyl ketone and dimethyl-formamide. The ester is hydrolyzed using standard synthetic methods, such as by reaction of the alkylated intermediate with an aqueous acid or base. For example, the ethyl ester is readily hydrolyzed by reaction with 5N sodium hydroxide in a water miscible organic solvent, such as methanol. Acidification of the reaction with concentrated hydrochloric acid produces the Formula III compound, wherein $R^6$ is hydroxyl, as the hydrochloride salt.

The Formula III compounds, wherein $R^6$ is chloro or bromo, are prepared by halogenating the Formula III compounds wherein $R^6$ is hydroxyl. Suitable halogenating agents include oxalyl chloride, thionyl chloride, thionyl bromide, phosphorous tribromide, triphosgene, and phosgene. Preferably, $R^6$ is chloro. Suitable solvents for this reaction include methylene chloride, 1,2-dichlorobenzene, chlorobenzene, and 1,2-dichloroethane. Preferably, the halogenation reaction is carried out in the same solvent as the subsequent acylation reaction. A catalytic amount of dimethylformamide, from about 0.05 to about 0.25 equivalents, is added to the chlorination reaction. When the reaction is carried out in 1,2-dichloroethane, the reaction is complete after about 2 to 5 hours at about 47° C. The Formula III compounds, wherein $R^6$ is chloro, may be stored as a solid, or as a solution or mixture in methylene chloride, chlorobenzene, 1,2-dichlorobenzene, or 1,2-dichloroethane. Preferably, the chlorination reaction and acylation reaction are carried out successively in the same reaction vessel.

The 2-aryl-6-hydroxy-3-[4-(2-aminoethoxy)benzoyl[b]-thiophenes can be prepared by acylation and subsequent dealkylation of the phenolic groups in two distinct steps, or sequentially in a "one-pot" reaction. The step-wise synthesis is described in the following paragraphs.

The acylated benzothiophene intermediate, a Formula IV compound, is prepared as shown in Scheme III, wherein $R^4$, $R^5$, $R^6$, and HX are as defined above.

Scheme III

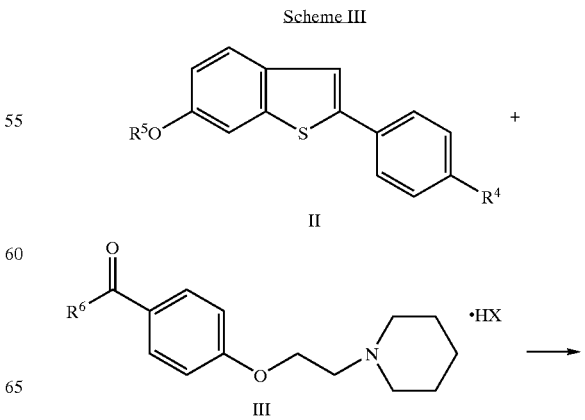

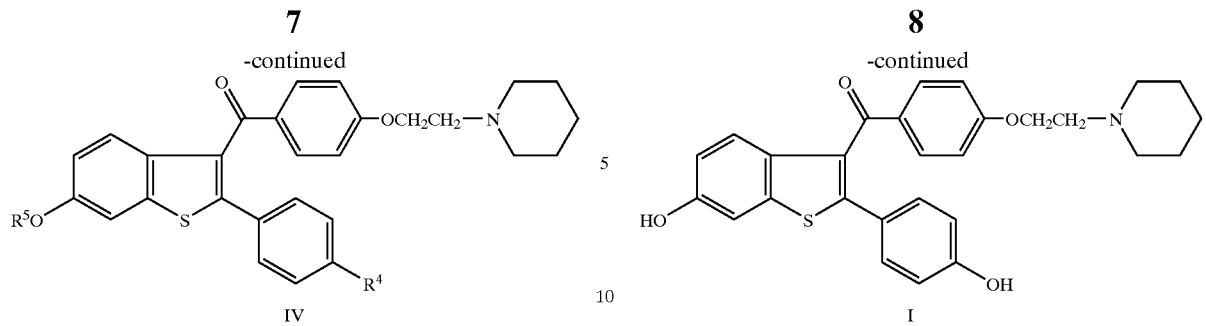

Generally, benzothiophene intermediate II is acylated with a Formula III compound, using boron trichloride or boron tribromide as the acylation catalyst. The reaction is carried out in an organic solvent, such as chlorobenzene, methylene chloride, 1,2-dichloroethane, 1,2-dichlorobenzene, bromobenzene, chloroform, 1,1,2,2-tetrachloro-ethane, 1,2,3-trichloropropane, and fluorobenzene. Preferably, the acylation is carried out in methylene chloride, chloro-benzene, or 1,2-dichloroethane. Most preferably, the acylation step is carried out in methylene chloride. The rate of acylation of the Formula II compound and the rate of dealkylation of the phenolic ethers of the Formula II and IV compounds varies with the choice of solvent, temperature of reaction, and choice of boron trihalide. Because the Formula II compounds having one or more unprotected phenolic groups will not acylate readily under these conditions, the amount of dealkylation must be minimized. Because boron tribromide is more preferred for dealkylation of phenolic ethers, the preferred boron trihalide for catalyzing acylation is boron trichloride. For boron trichloride-catalyzed reactions in methylene chloride, the acylation reaction can be performed at room temperature, with minimal dealkylation of the Formula II and IV compounds. In other solvents, the acylation reaction is carried out at lower temperatures, such as −10° C. to 10° C., to minimize the amount of dealkylation of the reaction starting material and product. When $R^6$ is chloro, at least 2 molar equivalents of the boron trihalide reagent are required for acylation. When the benzoic acid is used as an acylating agent ($R^6$=OH), five equivalents of the boron trihalide are typically used. The Formula IV compound may be isolated as the hydrochloride or hydrobromide salt, or as the free base.

In the step-wise process, the acylated intermediate (Formula IV compound) is dealkylated to produce the Formula I compound as shown in Scheme IV, wherein $R^4$, $R^5$, and HX are as defined above.

Scheme IV

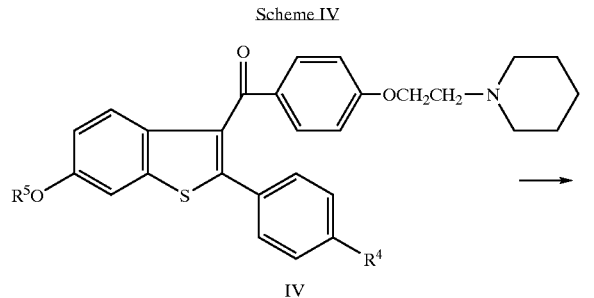

The Formula I compound is produced by reacting the hydrochloride or hydrobromide salt of the Formula IV compound with boron tribromide or boron trichloride. The preferred boron trihalide for dealkylation is boron tribromide. This dealkylation reaction can be carried out in a variety of organic solvents, such as methylene chloride, chlorobenzene, 1,2-dichloroethane, chloroform, 1,1,2,2-tetrachloroethane, 1,2,3-trichloropropane, 1,2-dichlorobenzene, and fluorobenzene. The preferred solvent is 1,2-dichloroethane. When the acid addition salt is used as a starting material, the amount of by-product resulting from dealkylation of the aminoethyl group is minimized. When methylene chloride is used as the solvent and the boron reagent is boron trichloride, the reaction is generally carried out at a temperature of about 55° C. to about 75° C., producing the Formula I compound with no detectable cleavage of the aminoethyl group. In other solvents, such as chloroform, 1,2-dichloroethane, chlorobenzene, 1,2-dichlorobenzene, and fluorobenzene, the dealkylation occurs readily at ambient temperatures. For example, when 1,2-dichloroethane is the solvent, the reaction is generally carried out at 25° C. to 35° C. with no detectable cleavage of the aminoethyl group. At least four equivalents of the boron trihalide reagent are typically used for complete reaction within a reasonable time.

Preferably, the Formula I compounds are prepared by a "one-pot" synthesis from the Formula II and III compounds as shown in Scheme V, wherein $R^4$, $R^5$, $R^6$, and HX are as defined above.

Scheme V

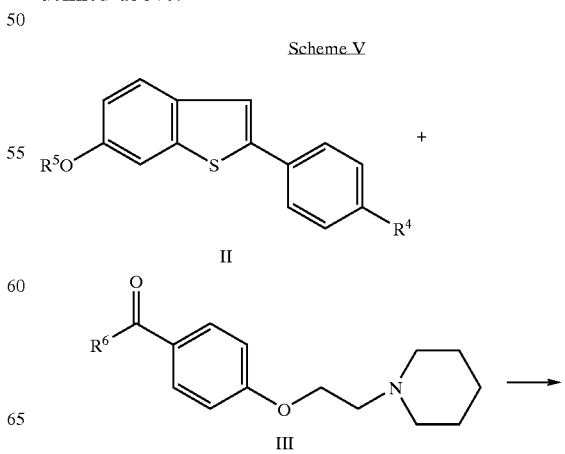

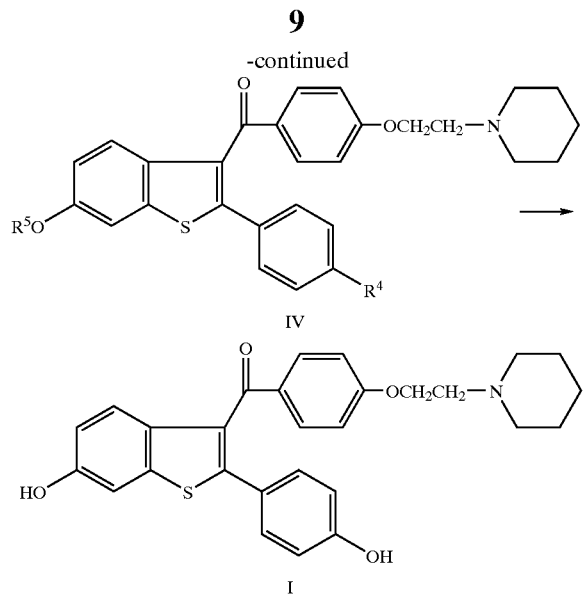

The benzothiophene Formula II compound is acylated with the Formula III compound in the presence of boron trichloride or boron tribromide; boron trichloride is preferred for the "one-pot" process. The reaction can be carried out in a variety of organic solvents, such as chloroform, methylene chloride, 1,2-dichloroethane, 1,2,3-dichloropropane, 1,1,2,2-tetrachloroethane, 1,2-dichlorobenzene, chlorobenzene, and fluorobenzene. The preferred solvent for this synthesis is 1,2-dichloroethane. The reaction is carried out at a temperature of about −10° C. to about 25° C., preferably at 0° C. The reaction is best carried out at a concentration of the benzothiophene Formula II compound of about 0.2 M to about 1.0 M. The acylation reaction is generally complete after about two hours to about eight hours.

The acylated benzothiophene, the Formula IV compound, is converted to a Formula I compound without isolation. This conversion is performed by adding additional boron trihalide and heating the reaction mixture. Preferably, two to five molar equivalents of boron trichloride are added to the reaction mixture, most preferably three molar equivalents. This reaction is carried out at a temperature of about 25° C. to about 40° C., preferably at 35° C. The reaction is generally complete after about 4 to 48 hours. The acylation/dealkylation reaction is quenched with an alcohol or a mixture of alcohols. Suitable alcohols for use in quenching the reaction include methanol, ethanol, and isopropanol. Preferably, the acylation/dealkylation reaction mixture is added to a 95:5 mixture of ethanol and methanol (3A). The 3A ethanol can be at room temperature or heated to reflux, preferably at reflux. When the quench is performed in this manner, the Formula I compound conveniently crystallizes from the resulting alcoholic mixture. Generally, 1.25–3.75 mL of alcohol per millimole of the benzothiophene starting material are used.

The preparation of a solvate of the Formula I compound, wherein HX is HCl, was described previously. Jones et al., J. Med. Chem., 27, 1057 (1984). The crystalline product of this "one-pot" process, when BCl$_3$ is used, is isolated as the solvate of the hydrochloride salt. These crystalline solvates are obtained under a variety of conditions. Generally, the form of the product of the present process is determined by choice of acylation/dealkylation solvent, boron trihalide, and work-up conditions.

A particularly useful solvate of the formula I compound is the 1,2-dichloroethane solvate. This solvate is prepared by carrying out the "one-pot" acylation/dealkylation process in 1,2-dichloroethane. When HX is HCl, the 1,2-dichloroethane solvate of a compound of formula I can exist in two distinct forms. One crystalline solvate form, termed crystal form I, is prepared by quenching the boron trichloride-catalyzed acylation/dealkylation reaction with ethanol. Preferably, a mixture of ethanol and methanol (95:5) is used in the preparation of this crystal form. This particular crystal form is characterized by the X-ray diffraction pattern shown in Table 1.

TABLE 1

X-ray Diffraction Pattern for Crystal Form 1.

| d-line spacing (Angstroms) | I/I$_o$ (×100) |
| --- | --- |
| 16.1265 | 3.80 |
| 10.3744 | 8.63 |
| 8.3746 | 5.29 |
| 7.9883 | 36.71 |
| 7.2701 | 5.06 |
| 6.5567 | 70.77 |
| 6.2531 | 6.79 |
| 5.5616 | 24.05 |
| 5.3879 | 100.00 |
| 5.0471 | 89.64 |
| 4.7391 | 85.96 |
| 4.6777 | 39.36 |
| 4.6332 | 62.60 |
| 4.5191 | 77.56 |
| 4.2867 | 36.82 |
| 4.2365 | 41.66 |
| 4.1816 | 49.60 |
| 4.0900 | 11.28 |
| 3.9496 | 11.85 |
| 3.7869 | 36.25 |
| 3.7577 | 56.16 |
| 3.6509 | 40.62 |
| 3.5751 | 15.65 |
| 3.5181 | 21.52 |
| 3.4964 | 18.53 |
| 3.4361 | 33.60 |
| 3.3610 | 6.21 |
| 3.3115 | 4.95 |
| 3.2564 | 7.36 |
| 3.2002 | 3.80 |
| 3.1199 | 15.77 |
| 3.0347 | 14.84 |
| 2.8744 | 9.67 |
| 2.8174 | 10.82 |
| 2.7363 | 11.51 |

The amount of 6-hydroxy-2-(4-hydroxyphenyl)-3-[4-(2-piperidinoethoxy)benzoyl]benzo[b]thiophene hydrochloride present in the crystalline material is about 87.1%, as determined using the high performance liquid chromatography (HPLC) assay described below. The amount of 1,2-dichloroethane present in the crystalline material is about 0.55 molar equivalents, as determined by proton nuclear magnetic resonance spectroscopy.

A large, analytically pure single crystal of the form I 1,2-dichloroethane solvate was prepared for single crystal X-ray analysis. This single crystal was prepared by placing a saturated methanolic solution of 6-hydroxy-2-(4-hydroxyphenyl)-3-[4-(2-piperidinoethoxy)benzoyl]benzo[b]thiophene hydrochloride in an atmosphere saturated with 1,2-dichloroethane (see Example 8). A total of 8419 reflections with 2θ less than 116° were collected, and used to solve the structure. The X-ray structure clearly shows that the crystalline material is a 1,2-dichloroethane solvate having a 1:2 ratio of solvent to solute molecules. The theoretical X-ray powder diffraction pattern spectrum, calculated from the single crystal X-ray data, is identical to that listed in Table 1, indicating that both solvates are identical.

A second crystalline solvate form, termed crystal form II, is similar to crystal form I. This second form is prepared by quenching the boron trichloride-catalyzed acylation/dealkylation reaction carried out in 1,2-dichloroethane with methanol. Alternatively, the boron trichloride-catalyzed acylation/dealkylation reaction using 1,2,3-trichloropropane as the solvent, produces a 1,2,3-trichloropropane solvate of this form. This particular crystal form is characterized by the X-ray diffraction pattern shown in Table 2.

TABLE 2

X-ray Diffraction Pattern for crystal Form II.

| d-line spacing (Angstroms) | $I/I_o$ (×100) |
|---|---|
| 10.4311 | 22.64 |
| 8.9173 | 10.73 |
| 8.4765 | 5.31 |
| 8.0095 | 50.39 |
| 7.3068 | 4.23 |
| 6.6094 | 79.23 |
| 5.6196 | 22.34 |
| 5.4223 | 89.86 |
| 5.1959 | 11.81 |
| 5.0746 | 74.90 |
| 4.8017 | 100.00 |
| 4.7262 | 57.97 |
| 4.6569 | 53.35 |
| 4.5378 | 96.75 |
| 4.4376 | 10.83 |
| 4.3397 | 56.89 |
| 4.2782 | 48.23 |
| 4.2129 | 40.94 |
| 4.1037 | 12.80 |
| 3.9880 | 14.76 |
| 3.8863 | 8.17 |
| 3.7999 | 42.13 |
| 3.7662 | 57.09 |
| 3.6738 | 38.58 |
| 3.5701 | 18.50 |
| 3.5393 | 19.00 |
| 3.4622 | 39.57 |
| 3.3867 | 5.02 |
| 3.3321 | 4.33 |
| 3.2686 | 6.79 |
| 3.1535 | 14.86 |
| 3.0450 | 13.58 |
| 2.9028 | 12.30 |
| 2.8302 | 19.59 |
| 2.7544 | 12.30 |
| 2.6366 | 6.89 |

The amount of 6-hydroxy-2-(4-hydroxyphenyl)-3-[4-(2-piperidinoethoxy)benzoyl]benzo[b]thiophene hydrochloride present in the crystalline material is about 86.8%. The amount of 1,2-dichloroethane present in the crystalline material is about 6.5%, as determined by gas chromatography.

The formula I compounds form a variety of distinct solvates with aromatic solvents. A useful aromatic solvate of this compound is the chlorobenzene solvate, which exists in a distinct form termed crystal form III. This particular crystal form is characterized by the X-ray diffraction pattern shown in Table 3.

TABLE 3

X-ray Diffraction Pattern for Crystal Form III.

| d-line spacing (Angstroms) | $I/I_o$ (×100) |
|---|---|
| 14.3518 | 7.24 |
| 10.3335 | 6.17 |
| 8.8305 | 4.29 |
| 7.9475 | 38.16 |
| 6.5904 | 64.25 |
| 6.2848 | 6.52 |
| 5.6048 | 28.06 |
| 5.4107 | 100.00 |
| 5.1544 | 11.26 |
| 5.0493 | 53.26 |
| 5.0224 | 46.11 |
| 4.8330 | 76.94 |
| 4.7694 | 34.23 |
| 4.6461 | 50.22 |
| 4.5754 | 38.61 |
| 4.4953 | 72.65 |
| 4.3531 | 49.15 |
| 4.2940 | 41.64 |
| 4.2425 | 35.75 |
| 4.1856 | 21.63 |
| 4.1338 | 9.47 |
| 4.0793 | 12.69 |
| 3.9960 | 18.50 |
| 3.9037 | 9.03 |
| 3.7854 | 40.39 |
| 3.7521 | 54.16 |
| 3.6787 | 28.60 |
| 3.6509 | 17.96 |
| 3.5444 | 31.72 |
| 3.4679 | 41.55 |
| 3.3899 | 7.69 |
| 3.3101 | 5.72 |
| 3.2561 | 7.42 |
| 3.1784 | 15.19 |
| 3.0445 | 11.17 |
| 3.0146 | 8.94 |
| 2.9160 | 11.89 |
| 2.8217 | 18.23 |
| 2.7500 | 12.06 |
| 2.6436 | 9.65 |
| 2.6156 | 6.97 |

The amount of 6-hydroxy-2-(4-hydroxyphenyl)-3-[4-(2-piperidinoethoxy)benzoyl]benzo[b]thiophene hydrochloride present in the crystalline material is about 78.6%. The amount of chlorobenzene present in the crystalline material is about 12.3%, as determined by HPLC.

A fourth crystalline solvated form is termed crystal form IV. This particular form is prepared by the boron trichloride-catalyzed acylation/dealkylation process using methylene chloride or chloroform as the solvent. This particular crystal form is characterized by the X-ray diffraction pattern shown in Table 4.

TABLE 4

X-ray Diffraction Pattern for Crystal Form IV.

| d-line spacing (Angstroms) | $I/I_o$ (×100) |
|---|---|
| 10.3696 | 14.40 |
| 8.9032 | 10.19 |
| 8.3125 | 7.61 |
| 7.9818 | 41.03 |
| 7.2036 | 7.34 |
| 6.5411 | 74.18 |
| 6.2367 | 6.39 |
| 5.5539 | 20.11 |

TABLE 4-continued

X-ray Diffraction Pattern for Crystal Form IV.

| d-line spacing (Angstroms) | I/I₀ (×100) |
|---|---|
| 5.3689 | 100.00 |
| 5.0272 | 95.92 |
| 4.7085 | 89.13 |
| 4.6406 | 73.37 |
| 4.6199 | 77.58 |
| 4.5347 | 69.70 |
| 4.4818 | 49.86 |
| 4.2589 | 47.69 |
| 4.2067 | 44.43 |
| 4.1659 | 44.16 |
| 4.0957 | 11.96 |
| 3.9347 | 11.28 |
| 3.7818 | 40.90 |
| 3.7614 | 53.53 |
| 3.6375 | 36.68 |
| 3.5773 | 20.11 |
| 3.5037 | 25.14 |
| 3.4409 | 32.34 |
| 3.4270 | 39.54 |
| 3.3088 | 12.64 |
| 3.2611 | 9.65 |
| 3.1046 | 12.77 |
| 3.0263 | 17.53 |
| 2.8536 | 8.29 |
| 2.8131 | 12.09 |
| 2.7309 | 8.97 |

The amount of 6-hydroxy-2-(4-hydroxyphenyl)-3-[4-(2-piperidinoethoxy)benzoyl]benzo[b]thiophene hydrochloride present in the crystalline material is about 80.4%, as determined by HPLC analysis. The amount of chloroform present in the crystalline material is about 0.42 molar equivalents, as determined by proton nuclear magnetic resonance spectroscopy.

A preferred crystalline form of 6-hydroxy-2-(4-hydroxyphenyl)-3-[4-(2-piperidinoethoxy)benzoyl]benzo[b]thiophene hydrochloride is a non-solvated crystal form. This particular form is preferred for use in the preparation of pharmaceutical formulations because of the absence of solvent that could affect the patient. This particular crystal form is prepared by recrystallization of the solvated hydrochloride salt produced by the boron trichloride-catalyzed acylation/dealkylation process. Generally, the solvated hydrochloride salt is added to a solution of sodium hydroxide in methanol or a mixture of methanol and water. At least one equivalent of base is used for dissolution and to ensure that the hydrochloride salt is converted to the free base. Activated carbon is optionally added to the resulting solution to facilitate removal of impurities. The mixture is filtered to remove the activated carbon, if present, and any insoluble impurities. The filtrate is extracted with an aliphatic hydrocarbon solvent, such as hexane or heptane, to remove the organic solvent used in the acylation/dealkylation reaction. The methanol solution is acidified with hydrochloric acid, such as gaseous or aqueous hydrochloric acid, causing crystallization of 6-hydroxy-2-(4-hydroxyphenyl)-3-[4-(2-piperidinoethoxy)benzoyl]benzo[b]thiophene as the non-solvated hydrochloride salt. The resulting crystalline slurry is preferably stirred at ambient temperature for about one to about two hours to ensure complete crystallization. The non-solvated crystalline form is isolated by filtration, followed by drying in vacuo. This particular crystal form is characterized by the X-ray diffraction pattern shown in Table 5.

TABLE 5

X-ray Diffraction Pattern for Non-solvated Crystal Form.

| d-line spacing (Angstroms) | I/I₀ (×100) |
|---|---|
| 13.3864 | 71.31 |
| 9.3598 | 33.16 |
| 8.4625 | 2.08 |
| 7.3888 | 7.57 |
| 6.9907 | 5.80 |
| 6.6346 | 51.04 |
| 6.1717 | 29.57 |
| 5.9975 | 5.67 |
| 5.9135 | 9.87 |
| 5.6467 | 38.47 |
| 5.4773 | 10.54 |
| 5.2994 | 4.74 |
| 4.8680 | 4.03 |
| 4.7910 | 5.98 |
| 4.6614 | 57.50 |
| 4.5052 | 5.75 |
| 4.3701 | 9.03 |
| 4.2516 | 69.99 |
| 4.2059 | 57.64 |
| 4.1740 | 65.07 |
| 4.0819 | 12.44 |
| 3.9673 | 22.53 |
| 3.9318 | 100.00 |
| 3.8775 | 9.07 |
| 3.7096 | 33.38 |
| 3.6561 | 21.65 |
| 3.5576 | 3.36 |
| 3.5037 | 7.97 |
| 3.4522 | 18.02 |
| 3.4138 | 4.65 |
| 3.2738 | 10.23 |
| 3.1857 | 8.90 |
| 3.1333 | 6.24 |
| 3.0831 | 9.43 |
| 3.0025 | 12.13 |
| 2.9437 | 4.96 |
| 2.8642 | 7.70 |
| 2.7904 | 11.95 |
| 2.7246 | 3.05 |
| 2.6652 | 3.32 |
| 2.5882 | 7.30 |

The amount of 6-hydroxy-2-(4-hydroxyphenyl)-3-[4-(2-piperidinoethoxy)benzoyl]benzo[b]thiophene hydrochloride present in the crystalline material is at least 95%.

This non-solvated crystalline material is more pure than the material produced by the processes described in the above-referenced patents. This material is free of aluminum impurities, as well as, chlorinated aliphatic hydrocarbon solvents and aromatic solvents. This non-solvated crystalline form is particularly preferred for use in the manufacture of pharmaceutical compositions.

The following examples further illustrate the processes described. The examples are not intended to be limiting to the scope of the invention in any respect, and should not be so construed. All experiments were run under positive pressure of dry nitrogen. All solvents and reagents were used as obtained. The percentages are generally calculated on a weight (w/w) basis; except for HPLC solvents which are calculated on a volume (v/v) basis. Proton nuclear magnetic resonance ($^1$H NMR) spectra were obtained on a Bruker AC-300 FTNMR spectrometer at 300.135 MHz. Melting points were determined by differential scanning calorimetry (DSC) in a TA Instrument DCS 2920 using a closed cell and a heating rate of 2° C./minute. The X-ray powder diffraction spectra were obtained in a Siemens D5000 X-Ray Powder Diffraktometer, using copper radiation and a Si(Li) detector.

The reactions were generally monitored for completion using high performance liquid chromatography (HPLC). The reaction producing the acid chloride, the Formula III compound wherein $R^6$ is chloro, was monitored using a Zorbax Rx-C8 column, (25 cm×4.6 mm ID, 5 µ particle) eluting with a mixture of 60 mM phosphate ($KH_2PO_4$) and 10 mM octanesulfonate (pH 2.0)/acetonitrile (60:40). The Formula III compound was derivatized with aniline, and analyzed using a carbanilide reference standard, derived from reaction of phosgene with aniline. A carbanilide standard stock solution was prepared by dissolving carbanilide (10 mg) and aniline (3 mL). This solution was diluted to a volume of 100 mL with the eluent described above. The reaction was monitored by the addition of about 0.3 mL of the acid chloride solution to 1 mL of HPLC grade methanol. The resulting mixture was shaken vigorously and allowed to derivatize. After 30 minutes, acetonitrile (6 mL) was added followed by dilution to 100 mL with the eluent described above.

The acylation, dealkylation, or acylation/dealkylation reactions are also monitored for completion by HPLC. A sample of the reaction mixture was assayed using a Zorbax Rx-C8 column, (25 cm×4.6 mm ID, 5 µ particle), eluting with a gradient as shown below:

| Gradient Solvent System | | |
| --- | --- | --- |
| Time (min.) | A (%) | B (%) |
| 0 | 60 | 40 |
| 5 | 60 | 40 |
| 10 | 45 | 55 |
| 20 | 38 | 62 |
| 25 | 45 | 55 |
| 32 | 45 | 55 |
| 37 | 60 | 40 |
| 42 | 60 | 40 |

A: 0.05 M $HClO_4$ (pH = 2.0)
B: acetonitrile

The reaction mixture was analyzed by diluting a 0.1 to 0.2 mL sample to 50 mL with a 60:40 mixture of A/B. Similarly, the mother liquor of the recrystallizations was sampled in a similar manner.

The amount (percentages) of 6-hydroxy-2-(4-hydroxyphenyl)-3-[4-(2-piperidinoethoxy)benzoyl]benzo[b]thiophene hydrochloride in the crystalline material (potency) was determined by the following method. A sample of the crystalline solid (5 mg) was weighed into a 100-mL volumetric flask, and dissolved in a 70/30 (v/v) mixture of 75 mM potassium phosphate buffer (pH 2.0) and acetonitrile. An aliquot of this solution (10 µL) was assayed by high performance liquid chromatography, using a Zorbax Rx-C8 column (25 cm×4.6 mm ID, 5 µ particle) and UV detection (280 nm). The following gradient solvent system is used:

| Gradient Solvent System (Potency) | | |
| --- | --- | --- |
| Time (min) | A (%) | B (%) |
| 0 | 70 | 30 |
| 12 | 70 | 30 |
| 14 | 25 | 75 |
| 16 | 70 | 30 |
| 25 | 70 | 30 |

A: 75 mM $KH_2PO_4$ buffer pH 2.0)
B: acetonitrile

The percentage of 6-hydroxy-2-(4-hydroxyphenyl)-3-[4-(2-piperidinoethoxy)benzoyl]benzo[b]thiophene hydrochloride in the sample is calculated using the peak area, slope (m), and intercept (b) of the calibration curve with the following equation:

$$\% \text{ potency} = \frac{\text{peak area} - b}{m} \times \frac{\text{sample volume (mL)}}{\text{sample weight (mg)}}$$

The amount (percentage) of solvent, such as methanol, ethanol, or 1,2-dichloroethane, present in the crystalline material is determined by gas chromatography. A sample of the crystalline solid (50 mg) was weighed into a 10-mL volumetric flask, and dissolved in a solution of 2-butanol (0.025 mg/mL) in dimethylsulfoxide. A sample of this solution was analyzed on a gas chromatograph using a DB Wax column (30 m×0.53 mm ID, 1 µ particle), with a column flow of 10 mL/min and flame ionization detection. The column temperature was heated from 35° C. to 230° C. over a 12 minute period. The amount of solvent was determined by comparison to the internal standard (2-butanol), using the following formula:

$$\% \text{ solvent} = \frac{C}{D} \times \frac{E}{F} \times \frac{G}{H} \times I$$

wherein:
C=ratio of solvent in sample
D=average ratio of standard for specific solvent
E=average weight of standard
F=weight of sample (mg)
G=volume of sample (10 mL)
H=volume of standard (10,000 mL)
I=purity of standard (%)

Preparation 1

6-Methoxy-2-(4-methoxyphenyl)benzo[b]thiophene

A solution of 3-methoxybenzenethiol (100 grams) and potassium hydroxide (39.1 grams) in water (300 mL) was added to denatured ethanol (750 mL), and the resulting mixture cooled to about 0° C. The cold mixture was treated with 4'-methoxyphenacyl bromide (164 grams) in several small portions. Upon complete addition, the mixture was cooled for an additional ten minutes, then allowed to warm to room temperature. After three hours, the mixture was concentrated in vacuo, and the residue treated with water (200 mL). The resulting mixture was treated with ethyl acetate, and the phases were separated. The organic phase was washed with water (2×), sodium bicarbonate solution (2×), and sodium chloride solution (2×). The organic phase was then dried over magnesium sulfate, filtered, and evaporated to dryness in vacuo to give 202 grams of α-(3-methoxyphenylthio)-4-methoxyacetophenone. This crude product was crystallized from methanol and washed with hexane to give 158 grams. Melting point 53° C.

Polyphosphoric acid (930 grams) was heated to 85° C. and treated with the intermediate product from above (124 grams) in small portions over 30 minutes. Upon complete addition, the resulting mixture was stirred at 90° C. After an additional 45 minutes, the reaction mixture was allowed to cool to room temperature. This mixture was treated with crushed ice while the mixture was cooled in an ice bath. The resulting mixture was treated with water (100 mL) producing a light pink precipitate. The precipitate was isolated by filtration, washed with water and methanol, and dried in vacuo at 40° C. to give 119 grams of 6-methoxy-2-(4-methoxyphenyl)benzo[b]thiophene. This crude product was slurried in hot methanol, filtered, and washed with cold methanol. The resulting solid material was recrystallized from ethyl acetate (4 liters), filtered, washed with hexane, and dried in vacuo to 68 grams of the title compound. Melting point 187–190.5° C.

Preparation 2

Ethyl 4-(2-Piperidinoethoxy)benzoate

A mixture of ethyl 4-hydroxybenzoate (8.31 g), 1-(2-chloroethyl)piperidine monohydrochloride (10.13 g), potassium carbonate (16.59 g), and methyl ethyl ketone (60 mL) was heated to 80° C. After one hour, the mixture was cooled to about 55° C. and treated with additional 1-(2-chloroethyl)piperidine mono-hydrochloride (0.92 g). The resulting mixture was heated to 80° C. The reaction was monitored by thin layer chromatography (TLC), using silica-gel plates and ethyl acetate/acetonitrile/triethylamine (10:6:1, v/v). Additional portions of 1-(2-chloroethyl)piperidine hydrochloride are added until the starting 4-hydroxybenzoate ester is consumed. Upon complete reaction, the reaction mixture was treated with water (60 mL) and allowed to cool to room temperature. The aqueous layer was discarded and the organic layer concentrated in vacuo at 40° C. and 40 mm Hg. The resulting oil was used in the next step without further purification.

Preparation 3

4-(2-Piperidinoethoxy)benzoic Acid Hydrochloride

A solution of the compound prepared as described in Preparation 2 (about 13.87 g) in methanol (30 mL) was treated with 5 N sodium hydroxide (15 mL), and heated to 40° C. After 4½ hours, water (40 mL) was added. The resulting mixture was cooled to 5–10° C., and concentrated hydrochloric acid (18 mL) was added slowly. The title compound crystallized during acidification. This crystalline product was collected by filtration, and dried in vacuo at 40–50° C. to give 83% yield of the title compound. Melting point 270–271° C.

Preparation 4

4-(2-Piperidinoethoxy)benzoyl Chloride Hydrochloride

A solution of the compound prepared as described in Preparation 3 (30.01 g) and dimethylformamide (2 mL) in methylene chloride (500 mL) was treated with oxalyl chloride (10.5 mL) over a 30–35 minute period. After stirring for about 18 hours, the reaction was assayed for completion by HPLC analysis. Additional oxalyl chloride may be added to the reaction if the starting carboxylic acid is present. Upon completion, the reaction solution was evaporated to dryness in vacuo. The residue was dissolved in methylene chloride (200 mL), and the resulting solution evaporated to dryness. This dissolution/evaporation procedure was repeated to give the title compound as a solid. The title compound may be stored as a solid or as a 0.2 M solution in methylene chloride (500 mL).

EXAMPLE 1

6-Methoxy-2-(4-methoxyphenyl)-3-[4-(2-piperidinoethoxy)benzoyl]-benzo[b]thiophene Hydrochloride A mixture of the compound prepared as described in Preparation 1 (8.46 grams) and the acid chloride prepared as described in Preparation 3 (10.0 grams) in methylene chloride (350 mL) was cooled to about 20–25° C. The cool mixture was treated with boron trichloride (2.6 mL), and the resulting mixture mechanically stirred. The reaction was monitored by HPLC using the assay described above. After 85 minutes, the in situ HPLC yield based on a 6-methoxy-2-(4-methoxyphenyl)-3-[4-(2-piperidinoethoxy)benzoyl]benzo[b]thiophene standard was 88%.

EXAMPLE 2

6-Hydroxy-2-(4-hydroxyphenyl)-3-[4-(2-piperidinoethoxy)benzoyl]-benzo[b]thiophene Hydrochloride 1,2-Dichloroethane Solvate (Crystal Form I)

A solution of 6-methoxy-2-(4-methoxyphenyl)-3-(4-(2-piperidinoethoxy)benzoyl]benzo[b]thiophene hydrochloride (2.0 g) in 1,2-dichloroethane (20 mL) was treated with boron trichloride (2.0 mL). The resulting mixture was stirred at 35° C. for about 18 hours. A mixture of ethanol and methanol (10 mL, 95:5, 3A) was treated with the reaction mixture from above, causing the alcoholic mixture to reflux. Upon complete addition, the resulting crystalline slurry was stirred at 25° C. After one hour, the crystalline product was filtered, washed with cold ethanol (10 mL), and dried at 40° C. in vacuo to give 1.78 g of the title compound. The X-ray powder diffraction pattern is identical to that reported in Table 1.

Potency: 80.2%.

1,2-Dichloroethane: 7.5% (gas chromatography).

EXAMPLE 3

6-Hydroxy-2-(4-hydroxyphenyl)-3-[4-(2-piperidinoethoxy)benzoyl]-benzo[b]thiophene Hydrochloride Methylene Chloride Solvate (Crystal Form IV)

A mixture of the compound prepared as described in Preparation 1 (7.54 grams) in methylene chloride (10 mL) and the acid chloride prepared as described in Preparation 4 (140 mL, 0.21 M solution in methylene chloride) was placed in a sealed reaction vessel (Hastalloy Parr). The solution was cooled to 0° C. and treated with boron trichloride (7.2 mL). The resulting reaction mixture was stirred at room temperature. After three hours, the reaction was cooled in an ice bath for 10 minutes. A second portion of boron trichloride (4.8 mL) was added to the reaction mixture, and the mixture was heated to 75° C. After 2.5 hours, the reaction mixture was cooled to about 15° C. The cool mixture was treated with tetrahydrofuran (15 mL) and methanol (45 mL). This mixture was stirred for about one hour at 18° C., producing a crystalline solid. The crystalline solid was removed by filtration, rinsed with cold methanol (45 mL), and dried in vacuo at 40° C. for 18 hours, to give 12.5 grams of the title compound. The X-ray powder diffraction pattern is identical to that reported in Table 4. Melting point 207° C.

Potency: 81.8%.

Methylene chloride: 0.4 molar equivalents ($^1$H NMR).

EXAMPLE 4

6-Hydroxy-2-(4-hydroxyphenyl)-3-[4-(2-piperidinoethoxy)benzoyl]-benzo[b]thiophene Hydrochloride 1,2-Dichloroethane Solvate (Crystal Form I)

A mixture of the compound prepared as described in Preparation 2 (15 g) and dimethylformamide (0.2 mL) in 1,2-dichloroethane (250 mL) was cooled to 0° C. Phosgene (8.25 mL) was condensed in a cold, jacketed addition funnel (−10° C.), and added to the cold mixture over a period of two minutes. The resulting mixture was heated to about 47° C. After about two and one half hours, the reaction was assayed by HPLC for completion. Additional phosgene may be added to drive the reaction to completion. Excess phosgene was removed by vacuum distillation at 30–32° C. and 105–110 mm Hg.

After about three to four hours, the reaction solution was treated with the compound prepared as described in Preparation 1 (13.52 g). The resulting solution was cooled to 0° C. Boron trichloride (12.8 mL) was condensed in a graduated cylinder, and added to the cold reaction mixture. After eight hours at 0° C., the reaction solution was treated with additional boron trichloride (12.8 mL). The resulting solution was heated to 30° C. After 15 hours, the reaction was monitored for completion by HPLC.

A mixture of ethanol and methanol (125 mL, 95:5, 3A) was heated to reflux, and treated with the reaction solution from above over a 60 minute period. Upon complete addition, the acylation/demethylation reaction flask was rinsed with additional ethanol (30 mL). The resulting slurry was allowed to cool to room temperature with stirring. After one hour at room temperature, the crystalline product was filtered, washed with ethanol (75 mL), and dried at 40° C. in vacuo to give 25.9 g of the title compound. The X-ray powder diffraction pattern is reported in Table 1. Melting point 261° C.

Potency: 87.1%.

1,2-Dichloroethane: 0.55 molar equivalents ($^1$H NMR).

EXAMPLE 5

6-Hydroxy-2-(4-hydroxyphenyl)-3-[4-(2-piperidinoethoxy)benzoyl]-benzo[b]thiophene Hydrochloride Chlorobenzene Solvate (Crystal Form 3)

A solution of the compound prepared as described in Preparation 1 (2.92 grams) and the acid chloride prepared as described in Preparation 4 (3.45 grams) in chlorobenzene (52 mL) was cooled to about 0° C. The cold solution was treated with boron trichloride (2.8 mL). The resulting mixture was mechanically stirred at about 0° C. After three hours, additional boron trichloride (2.8 mL) was added, and the reaction mixture was allowed to warm to room temperature. After about 16–20 hours, the reaction mixture was cooled to 0° C. The cold reaction was quenched by the slow addition of ethanol (26 mL) over 30 minutes. During the addition of the alcohol, a crystalline solid formed. Upon complete addition of the alcohol, the resulting mixture was stirred at room temperature for one hour. The crystalline solid was removed by filtration, washed with cold ethanol (25 mL), and dried in vacuo at 40° C. to give 5.94 grams of the title compound as a yellow solid. The X-ray powder diffraction pattern is identical to that reported in Table 3. Melting point 247° C.

Potency: 78.6%.

Chlorobenzene: 12.3% (HPLC).

EXAMPLE 6

6-Hydroxy-2-(4-hydroxyphenyl)-3-[4-(2-piperidinoethoxy)benzoyl]-benzo[b]thiophene Hydrochloride 1,2-Dichloroethane Solvate (Crystal Form II)

A mixture of the compound prepared as described in Preparation 1 (2.92 g), the compound prepared as described in Preparation 4 (3.45 g), and 1,2-dichloroethane (52 mL) was cooled to about 0° C. Boron trichloride gas was condensed into a cold graduated cylinder (2.8 mL), and added to the cold mixture described above. After eight hours at 0° C., the reaction mixture was treated with additional boron trichloride (2.8 mL). The resulting solution was heated to 35° C. After 16 hours, the reaction was complete.

Methanol (30 mL) was treated with the reaction mixture from above over a 20-minute period, causing the methanol to reflux. The resulting slurry was stirred at 25° C. After one hour, the crystalline product was filtered, washed with cold methanol (8 mL), and dried at 40° C. in vacuo to give 5.14 g of the title compound. The X-ray powder diffraction pattern is reported in Table 2. Melting point 225° C.

Potency: 86.8%.

1,2-Dichloroethane: 6.5% (gas chromatography).

EXAMPLE 7

6-Hydroxy-2-(4-hydroxyphenyl)-3-[4-(2-piperidinoethoxy)benzoyl]-benzo[b]thiophene Hydrochloride The compound prepared as described in Example 4 (4.0 grams) and activated carbon (0.4 grams, Darco G-60, Aldrich Chem. Co., Inc., Milwaukee, Wis.) were slurried in methanol (50 mL) at room temperature. The resulting mixture was treated with a solution of sodium hydroxide (0.313 grams) in methanol (10 mL). After 30 minutes, the slurry was filtered through Whatman #1 filter paper precoated with diatomaceons earth (Hyflo Super Cel®, Aldrich Chem. Co.). The filter cake was rinsed with methanol (5 mL). The combined filtrate was treated (dropwise) with 2N hydrochloric acid (4 mL). The resulting slurry was stirred for 30 minutes at room temperature, then cooled to about 9° C. After one hour, the cool mixture was filtered. The filter cake was rinsed with cold methanol (10 mL, 0° C.), and dried in vacuo at 60° C. for about 18 hours to give 2.06 grams of an off-white free flowing powder.

Potency: 96.8%.

Related substances: 1.41%.

EXAMPLE 8

6-Hydroxy-2-(4-hydroxyphenyl)-3-[4-(2-piperidinoethoxy)-benzoyl]benzo[b]thiophene Hydrochloride 1,2-Dichloroethane Solvate (Crystal Form II)

A saturated solution of 6-hydroxy-2-(4-hydroxyphenyl)-3-[4-(2-piperidinoethoxy)benzoyl]benzo[b]thiophene hydrochloride was produced by stirring a slurry of the compound prepared as described in Example 7 in methanol at room temperature overnight. This mixture was filtered (Whatman #1 filter paper). A portion of the filtrate (20–25 mL) was placed in a 50 mL Erlenmeyer flask. This flask was placed within a glass jar (3.5 in.×4 in.) containing 1,2-dichloroethane (about 10 mL). The jar was sealed and the combination was allowed to stand at room temperature. After 24 hours, single crystals had crystallized from the methanol solution. These crystals were filtered and dried in vacuo. The crystal structure was determined with a Siemens R3m/V automated four-circle diffractometer using monochromatic copper radiation ($\lambda$=1.54178 Å). The crystal structure was solved using the direct methods routine TREF of the SHELXTL PLUS program library. Full-matrix least-squares refinement was conducted with anisotropic temperature factors for all atoms except hydrogens, which were included at calculated positions with isotropic temperature factors. The final R-factor was 8.02%. The crystal data is shown below.

| Crystal Data | |
|---|---|
| Space group | C2/C |
| Unit all dimensions | a = 20.720(7)Å |
| | b = 9.492(2)Å |
| | c = 28.711(4)Å |
| | $\beta$ = 96.50(2)° |
| Volume | 5610(2)Å$^3$ |
| Density (calc.) | 1.409 mg/m$^3$ |
| Absorption coefficient | 3.951 mm$^{-1}$ |

The X-ray structure clearly shows that the crystalline material is a 1,2-dichloroethane solvate having a 1:2 ratio of molecules of 1,2-dichloroethane to molecules of 6-hydroxy-2-(4-hydroxyphenyl)-3-[4-(2-piperidinoethoxy)benzoyl]-benzo[b]-thiophene hydrochloride.

EXAMPLE 9

6-Hydroxy-2-(4-hydroxyphenyl)-3-[4-(2-piperidinoethoxy)-benzoyl]benzo[b]thiophene Hydrochloride 1,2,3-Trichloropropane Solvate (Crystal Form II)

A mixture of the compound prepared as described in Preparation 1 (2.70 g), the compound prepared as described in Preparation 4 (3.60 g), and 1,2,3-trichloropropane (50 mL) was treated with boron trichloride (2.6 mL). After three hours at 20–25° C., the reaction mixture was treated with additional boron trichloride (2.6 mL). After about 18 hours, the reaction mixture was treated with tetrahydrofuran (15 mL) followed by the slow addition of methanol (15 mL). After these additions were complete, the resulting mixture was stirred at room temperature. After one hour, the crystalline solid was collected by filtration, washed with cold methanol (10 mL), and dried at 50° C. in vacuo to give 4.13 g of the title compound. The X-ray powder diffraction pattern was identical to that reported in Table 2. Melting point 236° C.

Potency: 78.9%.

1,2,3-Trichloropropane: 0.5 molar equivalents ($^1$H NMR).

EXAMPLE 10

6-Hydroxy-2-(4-hydroxyphenyl)-3-[4-(2-piperidinoethoxy)-benzoyl]benzo[b]thiophene Hydrochloride Chloroform Solvate (Crystal Form IV)

The title compound (4.42 g) was prepared using the procedure described in Example 9, except the reaction solvent was chloroform (50 mL). The X-ray powder diffraction pattern was identical to that reported in Table 4. Melting point 258° C.

Potency: 80.4%.

Chloroform: 0.42 molar equivalents ($^1$H NMR).

EXAMPLE 11

6-Hydroxy-2-(4-hydroxyphenyl)-3-[4-(2-piperidinoethoxy)-benzoyl]benzo[b]thiophene Hydrochloride A solution of sodium hydroxide (0.313 g) in methanol (10 mL) was diluted with additional methanol (50 mL). This solution was treated with the compound prepared as described in Example 6 (4.0 g). After 45 minutes at room temperature, the solution was filtered (Whatman #1 filter paper) and the filter paper rinsed with methanol (3 mL). The filtrate was treated with 2 N hydrochloric acid (4 mL), producing a crystalline slurry. After 1½ hours, this crystalline product was filtered, washed with methanol (5 mL), and dried at 45–50° C. in vacuo to give 2.103 g of the title compound. The X-ray powder diffraction pattern was identical to that reported in Table 5. Potency: 96.5%.

EXAMPLE 12

6-Hydroxy-2-(4-hydroxyphenyl)-3-[4-(2-piperidinoethoxy)-benzoyl]benzo[b]thiophene Hydrochloride A solution of sodium hydroxide (0.313 g) in methanol (10 mL) was diluted with additional methanol (40 mL) and water (10 mL). This solution was treated with the compound prepared as described in Example 5 (4.0 g). The resulting solution was extracted with hexane (2×50 mL) to remove the chlorobenzene. The methanolic phase was treated with 2 N hydrochloric acid (4 mL), producing a crystalline slurry. After one hour, the crystalline product was filtered, washed with methanol (5 mL), and dried at 60° in vacuo to give 2.23 g of the title compound. The X-ray powder diffraction pattern was identical to that reported in Table 5.

Often, compounds which have poor solubility profiles can have their bioavailability enhanced by increasing the surface area of the formulated particles. The surface area generally increases per unit volume as the particle size decreases. Various techniques for grinding or milling a drug substance are well known in the art and each of these techniques are commonly used to decrease particle size and increase the surface area of the particle. It would seem reasonable that the best way to deal with any slightly soluble compound would be to mill it to the smallest size possible; however, this is not always practical or desirable. The milling process has an economic cost not only it the direct cost of the process, itself, but also with other associated factors. For example, very finely divided material presents difficulties and cost in capsule filling or tablet preparation, because the material will not flow, but becomes caked in finishing machinery. Such finishing difficulties generate non-homogeneity in the final product, which is not acceptable for a drug substance. Additionally, the milling process, physically generates heat and pressure on the material, such conditions lead to chemical degradation of the compound, thus such milling techniques are usually kept to a minimum.

Therefore, there is always dynamic between the properties which yield the maximum bioavailability (particle surface area) and the practical limits of manufacture. The point of compromise which marks this "best solution" is unique to each situation and unique as to its determination.

Methods for determining the size of particles are known in the art. The following is a description of one method, but is not intended to be limiting. For example, the general method of U.S. Pat. No. 4,605,517 could be employed.

In preparing the particulate compound of the invention a compound of formula I, in its raw state, is first characterized for size using an instrument adapted to measure equivalent spherical volume diameter, that is to say a Horiba LA900 Laser Scattering Particle Size Distribution Analyzer or equivalent instrument. Typically a representative sample of a compound of formula I would be expected to comprise in its raw state particles having a mean equivalent spherical volume diameter of about 110–200 microns and with a broad size distribution.

After being characterized for size in its raw state, the raw compound is then milled, preferably using a pin mill under suitable conditions of mill rotation rate and feed rate, to bring the particle size value within the above mentioned limits according to the invention. The efficiency of the milling is checked by sampling using a Horiba LA900 Laser Scattering Particle Size Distribution Analyzer and the final particle size is checked in a similar manner. If the first pass through the mill does not produce the required size distribution, then one or more further passes are effected.

The compound of formula I in its particulate form within the above mentioned limits according to the invention may then be mixed with an excipient or carrier as necessary and, for example, compressed into tablets. Thus, for example, the particulate compound may be mixed with anhydrous lactose, lactose monohydrate, a portion of crospovidone and granulated in an aqueous dispersion of povidone and polysorbate 80. After drying and milling into granules the material can be terminally blended with magnesium stearate and remaining crospovidone to be compressed into tablets.

Because the particles in the raw state as well as after milling or other particle size reduction techniques are irregular in shape, it is necessary to characterize them not by measurement of an actual size such as thickness or length, but by measurement of a property of the particles which is related to the sample property possessed by a theoretical spherical particle. The particles are thus allocated an "equivalent spherical diameter".

The values found from characterizing a large number of "unknown" particles can be plotted frequency vs. diameter or in other methods weight vs. diameter, usually adopting percentage undersize values for frequency or weight. This gives a characteristic curve representing size distribution of the sample, i.e., cumulative percentage undersize distribution curve. Values from this can be read off directly or plotted on log-probability paper to give an appropriate straight line. The mean equivalent spherical volume diameter is the 50% undersize value.

The mean equivalent spherical volume diameter found is thus a statistical representation of a theoretical particle having the same property as the "unknown" particle.

As indicated above the mean equivalent sphere volume diameter of the particles of the milled compound of formula I may be evaluated using a Horiba LA900 Laser Scattering Particle Size Distribution Analyzer. Using such an instrument values for a suspension of the particle of unknown size may be obtained and the instrument may be monitored using a control sample having particles within the size range expected based on statistical analysis of the sample. Multiple runs of the control sample established the standard deviation in measurement of the mean to be 1.3 microns.

Following is a description by way of example of the preparation of compositions in accordance with the invention. In all of the Examples the compound was prepared from raw form using a pin mill and consisted of particles having a mean equivalent spherical volume diameter of between about 5 and 20 microns, at least 90% of the particles having a particle size of less than about 35 microns.

The particle size of the reduced raloxifene HCl was measured as follows. The laser scattering particle size distribution analysis was effected on a small sample of the reduced material which is suspended in approximately 180 ml of dispersant solution. Sample is added to the dispersant until an acceptable level of laser light obscuration achieved at which point the particle size distribution is measured. Prior to the sample suspension the dispersant solution was prepared by adding 20 drops of Coulter 1A dispersant to a saturated aqueous solution of raloxifene HCl. The dispersant solution was filtered through a 0.2 micron microporous membrane filter to provide the necessary particle-free suspending dispersant.

Within five minutes of the preparation of the dispersion, triplicate particle size measurements were performed. Triplicate measurements are effected as a minimum check a) to produce more reliable measurements and b) to check the equivalent sampling of the suspended material has been reproducible i.e., the suspension has not settled.

The results were automatically recorded and displayed graphically to give a frequency percentage vs. undersize and a cumulative percentage vs. undersize characteristic curves for the sample. From this, the mean equivalent spherical volume diameter value was derived (50% undersize value) together with the standard deviation of the distribution calculated as above.

Several physical properties of raloxifene hydrochloride have been investigated during the progression of the compound through development. These include particle size, surface area, and powder bulk density.

A primary determinant in the potential influence of such properties on drug product performance is the aqueous solubility of the drug substance. Raloxifene hydrochloride has a water solubility of approximately 0.3 mg/mL at 25° C. and significantly lower values in Simulated Gastric Fluid, USP (0.003 mg/mL) and Simulated Intestinal Fluid, USP (0.002 mg/mL) at 37° C. The aqueous value falls into the USP classification of "very slightly soluble", while according to the recent SUPAC guidance ("Industry Guidance Immediate Release Solid Oral Dosage Forms Pre- and Post-Approval Changes: Chemistry, Manufacturing and Controls, In Vitro Dissolution Testing, and In Vivo Bioequivalence Documentation", Prepared by the Immediate Release Scale-Up and Post Approval Change (SUPAC), Expert Working Group of the Chemistry Manufacturing Controls Coordinating Committee (CMC CC) of the Center for Drug Evaluation and Research at the FDA) on immediate release solid oral dosage forms, the compound has low solubility with a dose solubility volume of greater than 250 mL. Given the low solubility, the rate at which the dosage form dissolves in the gastrointestinal tract can potentially impact the rate and extent of absorption of the active compound. Two related physical properties of the bulk drug which can alter the dissolution rate of the dosage form are particle size and surface area. The impact of surface area which is a function of particle size is illustrated in the Noyes-Whitney equation given below.

$$dC/dt = (D/h)*(S)*(Cs-C)$$

Here, C is the concentration of drug at time t, D is the diffusion coefficient of drug in the medium, h is the thickness of diffusion layer, Cs is the saturation solubility of drug in the diffusion layer and S is the effective surface area of the drug particles. To ascertain the effect of particle size/surface area of raloxifene HCl on in vitro dissolution, lots with varying particle size distributions were obtained via recrystallization and further modified through various milling technologies. The following table contains pertinent data on four bulk lots produced in this effort, which includes particle size data generated utilizing laser light diffraction, and surface area data collected by nirogen adsorption, and analyzed through the BET (Brunauer, Emmett, Teller) equation.

TABLE 6

| Bulk Lot # | Milling Technology | Surface Area $m^2/gm$ | Mean Particle Size ($\mu m$) | 90% less than ($\mu m$) |
|---|---|---|---|---|
| #1 | Micronized | 6.09 | 3.9 | 6.8 |
| #2 | Recrystallized | 2.28 | 8.4 | 13.9 |
| #3 | Ball Milled | 2.10 | 23.3 | 55.3 |
| #4 | Slurry Milled | 0.45 | 48.1 | 89 |

These four bulk lots were handfilled into capsules to provide 60.0 mg of raloxifene hydrochloride and submitted for dissolution testing in a 0.1% aqueous polysorbate 80 medium utilizing USP Apparatus II, with a paddle speed of 50 rpm. Data was collected at 10, 20, 30 and 45 minutes to produce a dissolution profile.

TABLE 7

| Time (min.) Dissolved | % Dissolved | Time (min.) | % |
|---|---|---|---|
| Lot # 1 (micronized) | | Lot #2 (Control) | |
| 10 | 51 | 10 | 41 |
| 20 | 68 | 20 | 60 |
| 30 | 78 | 30 | 68 |
| 45 | 88 | 45 | 74 |
| Lot # 3 (Ball-milled) | | Lot #4 (Slurry Milled) | |
| 10 | 31 | 10 | 15 |
| 20 | 45 | 20 | 27 |
| 30 | 54 | 30 | 35 |
| 45 | 64 | 45 | 49 |

It was observed that a range of dissolution profiles resulted from the various particle size distributions of the bulk drug substance, with values ranging from 25% to approximately 80% dissolved at 30 minutes. In an attempt to evaluate these differences upon in vivo absorption, a study was conducted in Fischer 344 rats. In the study, rats were dosed with the same four bulk raloxifene lots in their diet (0.4% w/w) for seven days. Plasma concentrations of unconjugated raloxifene were quantitated by HPLC for the four bulk lots. The following table shows the excellent linear correlations obtained between the percent raloxifene hydrochloride dissolved at 10 minutes or 30 minutes in the in vitro dissolution test to the average area under the curve (AUC, ng-h/mL) values obtained in rats for each of the bulk drug lots.

TABLE 8

| Lot | # Dissolved at 10 Minutes | # Dissolved at 30 Minutes | AUC (ng-h/mL) |
|---|---|---|---|
| #1 - Micronized | 50 | 78 | 10056 |
| #2 - As Recrystallized | 41 | 68 | 8037 |
| #3 - Ball Milled | 31 | 55 | 5743 |
| #4 - Slurry Milled | 15 | 35 | 3329 |

This in vitro to in-vivo correlation supports the discriminating ability of the dissolution method, as well as emphasizing the need for a control strategy for either the particle size distribution or surface area of the bulk drug substance. Further evaluation of this data indicated that the particle size data correlates better to the differences noted in the dissolution data and in vivo absorption. This can be explained based upon the Noyes-Whitney equation, which relates dissolution to the effective surface area. It is postulated that the surface area as measured by nitrogen adsorption for the various types of milled raloxifene does not predict the effective surface area accessible to the dissolution medium. This is demonstrated when comparing the recrystallized (control) lot (lot #2) and ball milled lot (lot #3). While they have very similar surface area values, 2.28 and 2.10 $m^2/gm$ respectively, the control lot has a finer mean particle size, 8.4 microns compared to 23.3 microns for the ball milled lot. SEM photomicrographs of the ball milled particles show very irregular surfaces with numerous cracks and fissures which would result in increased surface area as measured by nitrogen adsorption, but may not provide surface area accessible to the dissolution medium, resulting in a lower effective surface area. This reasoning can explain the better correlation of the differences in particle size to the differences in in vitro dissolution and in vivo absorption, compared to the similarity of the surface areas for the two lots. Based upon these findings, the decision was made to pursue particle size distribution as a control parameter to ensure consistent performance of the drug product with regards to release of the drug component.

To further investigate the impact of particle size of raloxifene HCl on drug product performance as measured by in vitro dissolution and in vivo absorption, a single dose, plasma concentration versus time study was designed in cynomolgus monkeys. The study compared absorption from two bulk lots of raloxifene which possessed mean particle sizes of 48.1 and 9.0 microns. The lots were formulated into granulation matrices representative of granulations being compacted into tablets for human use. In addition, the bulk lot with the 9.0 mean particle size was generated through pin milling technology which represents the desired commercial milling route. The table below summarizes the particle size data of the two bulk lots.

TABLE 9

| Bulk Lot/ Granulation Lot # | Milling Technology | 10% Less Than $\mu m$ | 50% Less Than $\mu m$ | 90% Less Than $\mu m$ | Mean Particle Size |
|---|---|---|---|---|---|
| Lot 5A | Slurry | 11.4 | 44.1 | 90 | 48.1 |
| Lot 5B | Pin | 3.2 | 8.6 | 15.1 | 9.0 |

For the purposes of producing a dissolution profile, the granulations were handfilled into capsules to provide the equivalent of 60 mg of raloxifene hydrochloride. The dissolution data produced in 0.1% aqueous Tween medium, utilizing the paddle method at 50 rpm, are shown below.

TABLE 10

| Time (min.) | % Dissolved |
|---|---|
| Lot 5A (slurry milled) | |
| 10 | 33 |
| 20 | 55 |
| 30 | 65 |
| 45 | 74 |
| Lot 5B (pin milled) | |
| 10 | 63 |
| 20 | 91 |
| 30 | 95 |
| 45 | 97 |

These differences in particle size distribution again produced significant differences in the dissolution profile in the aqueous 0.1% polysorbate 80 dissolution medium in the study monkeys received each formulation according to a crossover study design and incorporating a replicate period to allow for intrasubject variability. The following Table 11 shows the mean average plasma concentrations of total raloxifene after the administration of a 25 mg/kg oral dose to the monkeys.

TABLE 11

| Lot 5A (slurry milled) | |
|---|---|
| Time (hrs.) | ng Total Raloxifene/ml plasma |
| 1.4 | 78 |
| 3.6 | 67 |
| 8.2 | 81 |
| 12.1 | 60 |
| 24.3 | 45 |
| 30 | 32 |
| 36.4 | 22 |
| 48.6 | 14 |

| Lot 5B (pin milled) | |
|---|---|
| Time (hrs.) | ng Raloxifene/ml plasma |
| 1.4 | 108 |
| 3.6 | 84 |
| 8.2 | 121 |
| 12.1 | 95 |
| 24.3 | 70 |
| 30 | 51 |
| 36.4 | 34 |
| 48.6 | 23 |

As seen from the plasma concentration versus time profiles given in Table 11, the formulation with the finer particle size bulk drug substance provided higher plasma concentrations of total raloxifene at all of the timepoints sampled. The superior absorption from the formulation with the finer particle size is reflected in both the rate and extent of absorption as illustrated in the following summary of pharmacokinetic parameters from the study.

| Lot Number | Cmax (ng/mL) | AUC (ng-h/mL) |
|---|---|---|
| 5A (9.0 microns) | 131 | 3608 |
| 5B (48.1 microns) | 96 | 2357 |

The differences shown were found to be significant upon statistical analysis (AUC, $p<0.005$ and Cmax, $p<0.02$). This data is further evidence of the critical nature of the particle size distribution on its impact on bioavailability. The study also confirms the discriminating ability of the in vitro dissolution method and its relationship to in vivo absorption. Once again, the differences observed in the in vitro dissolution profiles translated into in vivo absorption differences.

Based upon the above work and physical property data generated, a particle size specification was established. The invention provides that the mean particle size, as determined by laser light diffraction, should be less than about 25 microns. In addition, 90% of the particles by volume should be under 50 microns, which allows for characterization of the distribution. Preferably, the size is between about 5 and about 20 microns, and 90% of the particles have a size of less than about 35 microns. To justify this range, bulk lots were produced by pin milling and samples of the available extremes were manufactured into formulated tablets and in vitro dissolution testing. In one study, six bulk lots of raloxifene hydrochloride (ca. 1 kg) were received and manufactured into formulated 60 mg raloxifene HCl tablets representative of the tablets being utilized in Phase III clinical testing. The particle size data for the lots utilized is summarized in the following Table 12.

TABLE 12

(all particle size in microns)

| Lot # | 10% Less Than | 50% Less Than | 90% Less Than | Mean |
|---|---|---|---|---|
| 6 | 2 | 6 | 12 | 6 |
| 7 | 3 | 8 | 21 | 10 |
| 8 | 3 | 11 | 31 | 15 |
| 9 | 3 | 12 | 30 | 14 |
| 10 | 2 | 5 | 10 | 6 |
| 11 | 3 | 9 | 23 | 11 |

The dissolution profile in 0.1% aqueous polysorbate 80 for all of these 6 bulk lots formulated into tablets are comparable in all cases. In addition, all lots displayed a relatively fast dissolution profile, with values greater than 90% dissolved at 20 minutes. To statistically assess the dissolution as a function of particle size, JMP Statistical and Graphics Guide software (SAS Institute, Inc., Cary, N.C.) was utilized and a plot was generated where the percent dissolved at 20 minutes was plotted as a function of the average particle size of each lot. Table 13 sets out the data.

TABLE 13

% Dissolved - Raloxifene Hydrochloride from Core Tablets

| Time (Min) | Lot Number | | | | | |
|---|---|---|---|---|---|---|
| | 6 | 7 | 8 | 9 | 10 | 11 |
| 10 | 89.2 | 88.1 | 81.1 | 74.5 | 84.1 | 80.5 |
| 20 | 92.3 | 92.6 | 95.4 | 91.3 | 96.0 | 93.7 |
| 30 | 93.2 | 93.9 | 97.0 | 93.3 | 96.3 | 94.0 |
| 45 | 93.0 | 94.1 | 98.4 | 93.9 | 96.1 | 94.6 |

The scatter observed in the plot, along with the high p-value (0.81) support the conclusion of a non-significant effect of particle size on dissolution over this range of particle sizes. Similar analyses were performed at the other timepoint, 10, 30 and 45 minutes, with calculated p-values of 0.11, 0.76, and 0.40 respectively. These high p-values along with the observation of both negative and positive slopes at the various timepoints again support the appropriateness of the range for the particle size.

Another similar study was performed with 7 different particle size distributions of bulk drug, with each again being formulated into 60 mg tablets. The particle size data for these lots is summarized in Table 14.

TABLE 14

(all particle size in microns)

| Lot | 10% Less Than | 50% Less Than | 90% Less Than | Mean |
|---|---|---|---|---|
| 70B | 3.3 | 14.5 | 39.3 | 18.8 |
| 70E | 2.8 | 10.5 | 26.3 | 13.0 |
| 70F | 3.4 | 16.0 | 50.2 | 22.9 |
| 71B | 3.1 | 12.9 | 38.9 | 17.8 |
| 71D | 2.8 | 10.1 | 25.6 | 12.6 |
| 71G | 3.3 | 14.6 | 42.1 | 19.6 |
| 71H | 2.9 | 11.1 | 28.2 | 13.7 |

The dissolution data collected in 0.1% aqueous polysorbate 80 for these seven bulk lots formulated into tablets is given in the following table.

TABLE 15

% Dissolved - Raloxifene Hydrochloride

| Time (Min) | Lot Number | | | | | | |
|---|---|---|---|---|---|---|---|
| | 70B | 70E | 70F | 71B | 71D | 71G | 71E |
| 10 | 76 | 81 | 73 | 76 | 75 | 61 | 68 |
| 20 | 94 | 96 | 91 | 93 | 88 | 85 | 91 |
| 30 | 98 | 99 | 95 | 98 | 91 | 88 | 95 |
| 45 | 99 | 99 | 97 | 99 | 97 | 97 | 98 |

As with the previous set of particle size distributions, the comparable dissolution profiles obtained with these particle size distributions support the ranges for particle size given in this invention.

Given the relationship shown between in vitro dissolution and in vivo absorption, it follows that the particle size distribution range claimed in this patent will provide surprisingly consistent in vivo absorption/bioavailability characteristics.

In addition to the role of particle size in vitro dissolution and in vivo absorption, another important aspect is its role on the various unit operations of the drug product manufacturing process. While the particle size specification ensures consistent delivery of the drug molecule to the sites of absorption in the gastrointestinal tract, it also allows for better control during the wet granulation step of the tablet manufacturing process. By controlling the particle size, the variations in quantity of water needed to elicit the appropriate progression of the granulation power consumption curve is reduced. By maintaining the particle size within the previous mentioned constraints, established quantities of water can be dictated in the manufacturing ticket for routine lot manufacture. The granulation step is common to many tablet and capsule manufacturing operations and is typically driven by the addition of water to bring about the desired endpoint of the granulation. A downstream unit operation dependent upon the granulation endpoint is the milling of the dried granulation and the resulting particle size distribution obtained on the granulation. It has been discovered that the incoming particle size of the active ingredient also effects the ultimate particle size distribution of the dry milled agglomerates formed during granulations. For a fixed water quantity, a coarser distribution will result in a finer size distribution of the dry milled agglomerates. Too fine a granulation distribution can lead to poor granulation flow and poor control of individual tablet weight during the compression step. Thus the narrow particle size constraints previously mentioned have also resulted in making the process more amenable to automation by reducing the variations in water required during the granulation step and producing dry milled granules of the appropriate distribution to prevent the rejection of tablets during compression due to unacceptable tablet weight.

The present invention also provides methods of use in inhibiting compounds of Formula I. Such uses include inhibiting osteoporosis, treating or prevent breast cancer, inhibiting uterine fibrosis, inhibiting endometriosis, and lowering serum cholesterol.

As used herein, the term "effective amount" means an amount of compound of formula I which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 10.0 mg to about 1000 mg/day of a compound of the present invention. Preferred daily doses generally will be from about 50 mg to about 150 mg/day.

Besides the hydrochloride salt, the compounds of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, $\beta$-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisultate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. Of course, the preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The compounds of this invention can be administered by a variety of routes including oral, rectal, transdermal, subucutaneus, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well known and readily available ingredients. For example, the compounds of formula I, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate, sodium bicarbonate and cross-linked povidone (cross povidone); agents for retarding dissolution such as paraffin; resorption accelerators such as quaternary ammonium compounds; surface active agents such as cetyl alcohol, polysorbate 80, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I, alone or in combination with another pharmaceutical agent, generally will be administered in a convenient formulation. The following formulation examples only are illustrative and are not intended to limit the scope of the present invention.

Formulations

In the formulations which follow, "Raloxifene" means a compound of formula I, including salts and solvates thereof.
Formulation 1: Gelatin Capsules
Hard gelatin capsules are prepared using the following:

| Ingredient | Quantity (mg/capsule) |
| --- | --- |
| Raloxifene | 10.0–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:
Formulation 2: Tablets

| Ingredient | Quantity (mg/tablet) |
| --- | --- |
| Raloxifene | 2.5–1000 |
| Cellulose, microcrystalline | 200–650 |
| Silicon dioxide, fumed | 10–650 |
| Stearic acid | 5–15 |

The components are blended and compressed to form tablets.

Alternatively, tablets each containing 2.5–1000 mg of Raloxifene are made up as follows:
Formulation 3: Tablets

| Ingredient | Quantity (mg/tablet) |
| --- | --- |
| Raloxifene | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

Raloxifene, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:
Formulation 4: Suspensions

| Ingredient | Quantity (mg/5 ml) |
| --- | --- |
| Raloxifene | 0.1–1000 mg |
| Sodium carboxymethyl cellulose | 50 mg |
| Syrup | 1.25 mg |

-continued

| Ingredient | Quantity (mg/5 ml) |
|---|---|
| Benzoic acid solution | 0.10 mL |
| Flavor | q.v. |
| Color | q.v. |
| purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
|---|---|
| Raloxifene | 0.25 |
| Ethanol | 25.75 |
| Propellant 22 (Chlorodifluoromethane) | 70.00 |

Raloxifene is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
|---|---|
| Raloxifene | 250 |
| Saturated fatty acid glycerides | 2,000 |

Raloxifene is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
|---|---|
| Raloxifene | 50 mg |
| Isotonic saline | 1,000 mL |

The solution of Raloxifene is intravenously administered to a patient at a rate of about 1 mL per minute.

Formulation 8: Combination Capsule I

| Ingredient | Quantity (mg/capsule) |
|---|---|
| Raloxifene | 50 |
| Premarin | 1 |

-continued

| Ingredient | Quantity (mg/capsule) |
|---|---|
| Avicel pH 101 | 50 |
| Starch 1500 | 117.50 |
| Silicon Oil | 2 |
| Tween 80 | 0.50 |
| Cab-O-Sil | 0.25 |

Formulation 9: Combination Capsule II

| Ingredient | Quantity (mg/capsule) |
|---|---|
| Raloxifene | 50 |
| Norethylnodrel | 5 |
| Avicel pH 101 | 82.50 |
| Starch 1500 | 90 |
| Silicon Oil | 2 |
| Tween 80 | 0.50 |

Formulation 10: Combination Tablet

| Ingredient | Quantity (mg/capsule) |
|---|---|
| Raloxifene | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

Formulation 11:

| Ingredient | Quantity (mg/capsule) |
|---|---|
| Raloxifene HCl | 60–150 |
| Polyvinylpyrrolidone | 15.75 |
| Polysorbate 80 | 5.25 |
| Lactose Anhydrous | 264.62 |
| Cross-linked polyvinylpyrrolidone | 31.5 |
| Stearic Acid | 5.25 |
| Magnesium Stearate | 2.63 |

The mixture of raloxifene HCl, lactose, and a portion of the cross-linked polyvinylpyrrolidone is granulated with an aqueous solution of the polyvinylpyrrolidone and polysorbate 80. The granules are dried, reduced to a suitable size, and mixed with stearic acid, magnesium stearate, and remaining cross-linked polyvinylpyrrolidone. The mixture is compressed into individual tablets.

Formulation 12:

| Ingredient | Quantity (mg/capsule) |
|---|---|
| Raloxifene HCl | 60–150 |
| Polyvinylpyrrolidone | 15.75 |
| Polysorbate 80 | 5.75 |
| Lactose Anhydrous | 132.06 |
| Dextrose | 132.06 |
| Cross-linked | 31.5 |

-continued

| Ingredient | Quantity (mg/capsule) |
|---|---|
| polyvinylpyrrolidone | |
| Stearic Acid | 5.25 |
| Magnesium Stearate | 2.63 |

The mixture of raloxifene HCl, lactose anhydrous, dextrose, and a portion of the cross-linked polyvinylpyrrolidone is granulated with an alcoholic solution of polyvinylpyrrolidone and polysorbate 80. The granules are dried, reduced to a suitable size, and mixed with magnesium stearate, stearic acid, and remaining cross-linked polyvinylpyrrolidone. The mixture is compressed into individual tablets.

Formulation 13:

| Ingredient | Quantity (mg/capsule) |
|---|---|
| Raloxifene HCl | 60–150 |
| Hydroxypropyl Cellulose | 16.00 |
| Sodium Laurylsulfate | 10.00 |
| Dextrose | 154.00 |
| Cross-linked sodium carboxymethylcellulose | 16.00 |
| Magnesium Stearate | 4.00 |

The mixture of raloxifene HCl, dextrose, and cross-linked sodium carboxymethylcellulose is granulated with an aqueous solution of hydroxypropyl cellulose and sodium laurylsulfate. The granules are dried, reduced to a suitable size, and mixed with magnesium stearate. The mixture is compressed into individual tablets.

Formulation 14:

| Ingredient | Quantity (mg/capsule) |
|---|---|
| Raloxifene HCl | 30.00 |
| Lactose Anhydrous | 144.00 |
| Lactose, Hydrous spray Dried | 36.00 |
| Polyvinylpyrrolidone | 12.00 |
| Polysorbate 80 | 2.40 |
| Cross-linked polyvinylpyrrolidone | 14.40 |
| Magnesium Stearate | 1.20 |

The mixture of raloxifene HCl, lactose anhydrous, spray-dried hydrous lactose, and a portion of the cross-linked polyvinylpyrrolidone is granulated with an aqueous solution of polyvinylpyrrolidone and polysorbate 80. The granules are dried, reduced to a suitable size, and mixed with magnesium stearate and remaining cross-linked polyvinylpyrrolidone. The mixture is compressed into individual tablets yielding a tablet weight of 240 mg.

Formulation 15:

| Ingredient | Quantity (mg/capsule) |
|---|---|
| Raloxifene HCl | 30.00 |
| Lactose Anhydrous | 160.00 |
| Hydroxypropyl Cellulose | 11.00 |
| Poloxamer | 7.00 |
| Cross-linked sodium | 23.00 |

-continued

| Ingredient | Quantity (mg/capsule) |
|---|---|
| carboxymethylcellulose | |
| Stearic Acid | 2.00 |
| Magnesium Stearate | 4.00 |

The mixture of raloxifene HCl, anhydrous lactose, and cross-linked sodium carboxymethylcellulose is granulated with an aqueous solution of poloxamer and hydroxypropyl cellulose. The granules are dried, reduced to a suitable size, and mixed with stearic acid and magnesium stearate. The mixture is then compressed into individual tablets yielding a tablet weight of 240 mg.

Formulation 16:

| Ingredient | Quantity (mg/capsule) |
|---|---|
| Raloxifene HCl | 30.00 |
| Lactose | 89.00 |
| Dextrose | 89.00 |
| Hydroxypropyl methylcellulose | 10.00 |
| Sodium Laurylsulfate | 5.00 |
| Cross-linked sodium polyvinylpyrrolidone | 12.00 |
| Stearic Acid | 5.00 |

The mixture of raloxifene HCl, lactose, dextrose, and cross-linked polyvinylpyrrolidone is granulated with an aqueous solution of hydroxypropyl methylcellulose and sodium laurylsulfate. The granules are dried, reduced to a suitable size, and mixed with the stearic acid. The mixture is then compressed into individual tablets yielding a tablet weight of 240 mg.

Formulation 17:

| Ingredient | Quantity (mg/capsule) |
|---|---|
| Raloxifene HCl | 60.00 |
| Lactose Anhydrous | 156.00 |
| Polyvinylpyrrolidone | 7.20 |
| Polysorbate 80 | 7.20 |
| Cross-linked sodium polyvinylpyrrolidone | 7.20 |
| Magnesium Stearate | 2.40 |

The mixture of raloxifene HCl, lactose anhydrous, and cross-linked polyvinylpyrrolidone is granulated with an aqueous solution of polyvinylpyrrolidone and polysorbate 80. The granules are dried, reduced to a suitable size, and mixed with magnesium stearate. The mixture is then compressed into individual tablets yielding a tablet weight of 240 mg.

Formulation 18:

| Ingredient | Quantity (mg/capsule) |
|---|---|
| Raloxifene HCl | 60.00 |
| Lactose Anhydrous | 120.00 |
| Lactose, hydrous spray-dried | 30.00 |
| Polyvinylpyrrolidone | 12.00 |
| Polysorbate 80 | 2.40 |

-continued

| Ingredient | Quantity (mg/capsule) |
|---|---|
| Cross-linked sodium polyvinylpyrrolidone | 14.40 |
| Magnesium Stearate | 1.20 |

The mixture of raloxifene HCl, lactose anhydrous, spray-dried hydrous lactose, and a portion of the cross-linked polyvinylpyrrolidone is granulated with an aqueous solution of polyvinylpyrrolidone and polysorbate 80. The granules are dried, reduced to a suitable size, and mixed with magnesium stearate and remaining cross-linked polyvinylpyrrolidone. The mixture is then compressed into individual tablets yielding a tablet weight of 240 mg.

Formulation 19:

| Ingredient | Quantity (mg/capsule) |
|---|---|
| Raloxifene HCl | 60.00 |
| Mannitol | 77.00 |
| Dextrose | 73.00 |
| Hydroxypropyl methylcellulose | 7.00 |
| Polysorbate 80 | 4.00 |
| Sodium Starch Glycolate | 14.00 |
| Stearic Acid | 4.00 |
| Magnesium Stearate | 1.00 |

The mixture of raloxifene HCl, mannitol, dextrose, and sodium starch glycolate is granulated with an aqueous solution of polysorbate 80 and hydroxypropyl methylcellulose. The granules are dried, reduced to a suitable size, and mixed with stearic acid and magnesium stearate. The mixture is then compressed into individual tablets yielding a tablet weight of 240 mg.

Formulation 20:

| Ingredient | Quantity (mg/capsule) |
|---|---|
| Raloxifene HCl | 150.00 |
| Lactose Anhydrous | 41.00 |
| Lactose, hydrous spray-dried | 10.25 |
| Polyvinylpyrrolidone | 11.50 |
| Polysorbate 80 | 2.30 |
| Cross-linked sodium polyvinylpyrrolidone | 13.80 |
| Magnesium Stearate | 1.15 |

The mixture of raloxifene HCl, anhydrous lactose, hydrous spray-dried lactose, and a portion of the cross-linked polyvinylpyrrolidone is granulated with an aqueous solution of polyvinylpyrrolidone and polysorbate 80. The granules are dried, reduced to a suitable size, and mixed with magnesium stearate and the remaining cross-linked polyvinylpyrrolidone. The mixture is then compressed into individual tablets yielding a tablet weight of 230 mg.

Formulation 21:

| Ingredient | Quantity (mg/capsule) |
|---|---|
| Raloxifene HCl | 150.00 |
| Lactose, hydrous spray-dried | 56.00 |
| Polyvinylpyrrolidone | 7.00 |
| Polysorbate 80 | 1.20 |
| Cross-linked sodium polyvinylpyrrolidone | 13.80 |
| Magnesium Stearate | 2.00 |

The mixture of raloxifene HCl, hydrous spray-dried lactose, and a portion of the cross-linked polyvinylpyrrolidone is granulated with an aqueous solution of polyvinylpyrrolidone and polysorbate 80. The granules are dried, reduced to a suitable size and mixed with magnesium stearate and remaining cross-linked polyvinylpyrrolidone. The mixture is then compressed into individual tablets yielding a tablet weight of 230 mg.

Formulation 22:

| Ingredient | Quantity (mg/capsule) |
|---|---|
| Raloxifene HCl | 150.00 |
| Lactose, anhydrous | 52.40 |
| Polyvinylpyrrolidone | 11.50 |
| Polysorbate 80 | 4.60 |
| Polyethylene Glycol 8000 | 11.50 |

The mixture of raloxifene HCl and anhydrous lactose is granulated with an aqueous solution of polysorbate 80 and polyvinylpyrrolidone. The granules are dried, reduced to a suitable size, and mixed with the polyethylene glycol 8000. The mixture is then compressed into individual tablets yielding a tablet weight of 230 mg.

Capsules may be prepared using the ingredients and procedures as described below:

Formulation 23:

| Ingredient | Quantity (mg/capsule) |
|---|---|
| Raloxifene HCl | 30.00 |
| Lactose, hydrous spray-dried | 178.30 |
| Sodium laurylsulfate | 4.60 |
| Cross-linked polyvinylpyrrolidone | 9.20 |
| Hydroxypropyl methylcellulose | 6.90 |
| Colloidal Silicon Dioxide | 1.00 |

The mixture of raloxifene HCl, hydrous spray-dried lactose, and cross-linked polyvinylpyrrolidone is granulated with an aqueous solution of sodium laurylsulfate and hydroxypropyl methylcellulose. The granules are dried, reduced to a suitable size, and mixed with colloidal silicon dioxide. This mixture is then filled into Size 3 hard-shell gelatin capsules utilizing conventional encapsulating equipment, with each capsule containing 230 mg of the final mixture.

Formulation 24:

| Ingredient | Quantity (mg/capsule) |
| --- | --- |
| Raloxifene HCl | 60.00 |
| Lactose, hydrous spray-dried | 148.30 |
| Sodium laurylsulfate | 4.60 |
| Cross-linked polyvinylpyrrolidone | 9.20 |
| Hydroxypropyl methylcellulose | 6.90 |
| Colloidal Silicon Dioxide | 1.00 |

The mixture of raloxifene HCl, hydrous spray-dried lactose, and cross-linked polyvinylpyrrolidone is granulated with an aqueous solution of sodium laurylsulfate and hydroxypropyl methylcellulose. The granules are dried, reduced to a suitable size, and mixed with colloidal silicon dioxide. This mixture is then filled into Size 3 hard-shell gelatin capsules utilizing conventional encapsulating equipment, with each capsule containing 230 mg of the final mixture.

Formulation 25:

| Ingredient | Quantity (mg/capsule) |
| --- | --- |
| Raloxifene HCl | 150.00 |
| Lactose, hydrous spray-dried | 58.30 |
| Sodium laurylsulfate | 4.60 |
| Cross-linked polyvinylpyrrolidone | 9.20 |
| Hydroxypropyl methylcellulose | 6.90 |
| Colloidal Silicon Dioxide | 1.00 |

The mixture of raloxifene HCl, hydrous spray-dried lactose, and cross-linked polyvinylpyrrolidone is granulated with an aqueous solution of sodium laurylsulfate and hydroxypropyl methylcellulose. The granules are dried, reduced to a suitable size, and mixed with colloidal silicon dioxide. This mixture is then filled into Size 3 hard-shell gelatin capsules utilizing conventional encapsulating equipment, with each capsule containing 230 mg of the final mixture.

We claim:

1. A pharmaceutical composition comprising:

a) a compound of formula I

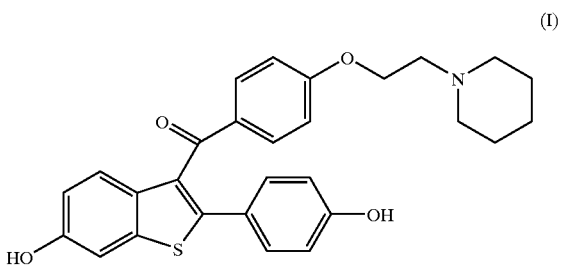

(I)

or a pharmaceutically acceptable salt or solvate thereof, characterized in that the compound of formula I is in particulate form, said particles having a mean particle size of less than about 25 microns, at least about 90% of said particles have a size of less than about 50 microns;

b) a surfactant; and c) a water-soluble diluent.

2. The composition of claim 1 wherein the compound is non-solvated crystalline 6-hydroxy-2-(4-hydroxy-phenyl)-3-[4-(-2-piperidinoethoxy)benzoyl]benzo[b]thiophene hydrochloride.

3. The composition of claim 2 wherein said particles have a mean particle size of between 5 and about 20 microns.

4. The composition of claim 3 wherein at least 90% of said particles have a size of less than about 35 microns.

5. The composition of claim 1 wherein the surfactant is polysorbate 80.

6. The composition of claim 2 wherein the surfactant is polysorbate 80.

7. The composition of claim 3 wherein the surfactant is polysorbate 80.

8. The composition of claim 4 wherein the surfactant is polysorbate 80.

9. The composition of claim 1 wherein the water-soluble diluent is lactose.

10. The composition of claim 2 wherein the water-soluble diluent is lactose.

11. The composition of claim 3 wherein the water-soluble diluent is lactose.

12. The composition of claim 4 wherein the water-soluble diluent is lactose.

13. The composition of claim 5 wherein the water-soluble diluent is lactose.

14. The composition of claim 6 wherein the water-soluble diluent is lactose.

15. The composition of claim 7 wherein the water-soluble diluent is lactose.

16. The composition of claim 8 wherein the water-soluble diluent is lactose.

17. The composition of claim 1 further comprising a hydrophilic binder.

18. The composition of claim 2 further comprising a hydrophilic binder.

19. The composition of claim 3 further comprising a hydrophilic binder.

20. The composition of claim 4 further comprising a hydrophilic binder.

21. The composition of claim 5 further comprising a hydrophilic binder.

22. The composition of claim 6 further comprising a hydrophilic binder.

23. The composition of claim 7 further comprising a hydrophilic binder.

24. The composition of claim 8 further comprising a hydrophilic binder.

25. The composition of claim 9 further comprising a hydrophilic binder.

26. The composition of claim 10 further comprising a hydrophilic binder.

27. The composition of claim 11 further comprising a hydrophilic binder.

28. The composition of claim 12 further comprising a hydrophilic binder.

29. The composition of claim 13 further comprising a hydrophilic binder.

30. The composition of claim 14 further comprising a hydrophilic binder.

31. The composition of claim 15 further comprising a hydrophilic binder.

32. The composition of claim 16 further comprising a hydrophilic binder.

33. The composition of claim 17 wherein the hydrophilic binder is polyvinylpyrrolidone.

34. The composition of claim 18 wherein the hydrophilic binder is polyvinylpyrrolidone.
35. The composition of claim 19 wherein the hydrophilic binder is polyvinylpyrrolidone.
36. The composition of claim 20 wherein the hydrophilic binder is polyvinylpyrrolidone.
37. The composition of claim 21 wherein the hydrophilic binder is polyvinylpyrrolidone.
38. The composition of claim 22 wherein the hydrophilic binder is polyvinylpyrrolidone.
39. The composition of claim 23 wherein the hydrophilic binder is polyvinylpyrrolidone.
40. The composition of claim 24 wherein the hydrophilic binder is polyvinylpyrrolidone.
41. The composition of claim 25 wherein the hydrophilic binder is polyvinylpyrrolidone.
42. The composition of claim 26 wherein the hydrophilic binder is polyvinylpyrrolidone.
43. The composition of claim 27 wherein the hydrophilic binder is polyvinylpyrrolidone.
44. The composition of claim 28 wherein the hydrophilic binder is polyvinylpyrrolidone.
45. The composition of claim 29 wherein the hydrophilic binder is polyvinylpyrrolidone.
46. The composition of claim 30 wherein the hydrophilic binder is polyvinylpyrrolidone.
47. The composition of claim 31 wherein the hydrophilic binder is polyvinylpyrrolidone.
48. The composition of claim 32 wherein the hydrophilic binder is polyvinylpyrrolidone.
49. The composition of claim 1 further comprising a lubricant and a disintegrant.
50. The composition of claim 2 further comprising a lubricant and a disintegrant.
51. The composition of claim 3 further comprising a lubricant and a disintegrant.
52. The composition of claim 4 further comprising a lubricant and a disintegrant.
53. The composition of claim 5 further comprising a lubricant and a disintegrant.
54. The composition of claim 18 further comprising a lubricant and a disintegrant.
55. The composition of claim 32 further comprising a lubricant and a disintegrant.
56. The composition of claim 48 further comprising a lubricant and a disintegrant.
57. The composition of claim 49 wherein said lubricant is magnesium stearate or stearic acid, and said disintegrant is cross-linked polyvinylpyrrolidone.
58. The composition of claim 50 wherein said lubricant is magnesium stearate or stearic acid, and said disintegrant is cross-linked polyvinylpyrrolidone.
59. The composition of claim 51 wherein said lubricant is magnesium stearate or stearic acid, and said disintegrant is cross-linked polyvinylpyrrolidone.
60. The composition of claim 52 wherein said lubricant is magnesium stearate or stearic acid, and said disintegrant is cross-linked polyvinylpyrrolidone.
61. The composition of claim 53 wherein said lubricant is magnesium stearate or stearic acid, and said disintegrant is cross-linked polyvinylpyrrolidone.
62. The composition of claim 54 wherein said lubricant is magnesium stearate or stearic acid, and said disintegrant is cross-linked polyvinylpyrrolidone.
63. The composition of claim 55 wherein said lubricant is magnesium stearate or stearic acid, and said disintegrant is cross-linked polyvinylpyrrolidone.
64. The composition of claim 56 wherein said lubricant is magnesium stearate or stearic acid, and said disintegrant is cross-linked polyvinylpyrrolidone.
65. The composition of claim 57 comprising the hydrochloride salt of a compound of formula I, polyvinylpyrrolidone, polysorbate 80, lactose, cross-linked polyvinylpyrrolidone, and magnesium stearate.
66. The composition of claim 58 comprising polyvinylpyrrolidone, polysorbate 80, lactose, cross-linked polyvinylpyrrolidone, and magnesium stearate.
67. The composition of claim 59 comprising polyvinylpyrrolidone, polysorbate 80, lactose, cross-linked polyvinylpyrrolidone, and magnesium stearate.
68. The composition of claim 60 comprising polyvinylpyrrolidone, polysorbate 80, lactose, cross-linked polyvinylpyrrolidone, and magnesium stearate.
69. The composition of claim 61 comprising polyvinylpyrrolidone, polysorbate 80, lactose, cross-linked polyvinylpyrrolidone, and magnesium stearate.
70. The composition of claim 62 comprising polyvinylpyrrolidone, polysorbate 80, lactose, cross-linked polyvinylpyrrolidone, and magnesium stearate.
71. The composition of claim 63 comprising polyvinylpyrrolidone, polysorbate 80, lactose, cross-linked polyvinylpyrrolidone, and magnesium stearate.
72. The composition of claim 64 comprising polyvinylpyrrolidone, polysorbate 80, lactose, cross-linked polyvinylpyrrolidone, and magnesium stearate.
73. The composition of claim 72 further comprising a film coating.

* * * * *

UNITED STATES PATENT AND TRADEMARK OFFICE
CERTIFICATE OF CORRECTION

PATENT NO.  : 6,797,719 B1
DATED       : September 28, 2004
INVENTOR(S) : Gordon Nelson Arbuthnot et al.

It is certified that error appears in the above-identified patent and that said Letters Patent is hereby corrected as shown below:

Column 41,
Line 39, "claim 5" should read -- claim 8 --.
Line 41, "claim 18" should read -- claim 16 --.

Signed and Sealed this

Twelfth Day of July, 2005

JON W. DUDAS
*Director of the United States Patent and Trademark Office*